(12) United States Patent
Lockard et al.

(10) Patent No.: US 8,414,607 B1
(45) Date of Patent: Apr. 9, 2013

(54) MINIATURE SHREDDING TOOL FOR USE IN MEDICAL APPLICATIONS AND METHODS FOR MAKING

(75) Inventors: Michael S. Lockard, Lake Elizabeth, CA (US); Uri Frodis, Los Angeles, CA (US); Adam L. Cohen, Los Angeles, CA (US); Richard T. Chen, Woodland Hills, CA (US); Pierre E. Dupont, Wellesley, MA (US); Pedro J. Del Nido, Lexington, MA (US); Nikolay V. Vasilyev, Belmont, MA (US)

(73) Assignees: Microfabrica Inc., Van Nuys, CA (US); Trustees of Boston University, Boston, MA (US); Children's Hospital Boston, Boston, MA (US)

(*) Notice: Subject to any disclaimer, the term of this patent is extended or adjusted under 35 U.S.C. 154(b) by 590 days.

(21) Appl. No.: 12/491,220

(22) Filed: Jun. 24, 2009

Related U.S. Application Data

(63) Continuation-in-part of application No. 12/490,295, filed on Jun. 23, 2009.

(60) Provisional application No. 61/075,007, filed on Jun. 24, 2008, provisional application No. 61/075,006, filed on Jun. 23, 2008, provisional application No. 61/164,864, filed on Mar. 30, 2009, provisional application No. 61/164,883, filed on Mar. 30, 2009.

(51) Int. Cl.
*A61B 17/32* (2006.01)

(52) U.S. Cl. .......................... 606/180; 606/84; 606/179

(58) Field of Classification Search .............. 606/79–85, 606/167–180; 604/22; 241/236
See application file for complete search history.

(56) References Cited

U.S. PATENT DOCUMENTS

| | | | |
|---|---|---|---|
| 2,259,015 A * | 10/1941 | Anderson et al. | ............... 83/852 |
| 2,455,655 A | 12/1948 | Carroll | |
| 3,404,677 A | 10/1968 | Springer | |
| 3,882,872 A | 5/1975 | Douvas et al. | |
| 3,937,222 A | 2/1976 | Banko | |
| 4,621,637 A | 11/1986 | Fishbein | |
| 4,747,821 A | 5/1988 | Kensey et al. | |
| 4,842,578 A | 6/1989 | Johnson et al. | |
| 4,844,363 A | 7/1989 | Garnier et al. | ............... 241/224 |
| 4,943,296 A | 7/1990 | Funakubo et al. | |

(Continued)

FOREIGN PATENT DOCUMENTS

WO    WO 2008/037984 A2    4/2008

OTHER PUBLICATIONS

Schmitz et al.; U.S. Appl. No. 13/007,578 entitled "Selective Tissue Removal Tool for Use in Medical Applications and Methods for Making and Using," filed Jan. 14, 2011.

(Continued)

*Primary Examiner* — Kathleen Holwerda
(74) *Attorney, Agent, or Firm* — Shay Glenn LLP

(57) ABSTRACT

The present invention relates generally to the field of microscale or millimeter scale devices and to the use of multi-layer multi-material electrochemical fabrication methods for producing such devices with particular embodiments relate to shredding devices and more particularly to shredding devices for use in medical applications. In some embodiments, tissue removal devices include tissue anchoring projections, improved blade configurations, and/or shields or shrouds around the cutting blades to inhibit outflow of tissue that has been brought into the device.

10 Claims, 20 Drawing Sheets

U.S. PATENT DOCUMENTS

| | | | |
|---|---|---|---|
| 5,019,088 A | 5/1991 | Farr | |
| 5,084,052 A | 1/1992 | Jacobs | |
| 5,141,168 A | 8/1992 | Pepper | 241/236 |
| 5,181,433 A | 1/1993 | Ueno | 74/409 |
| 5,190,637 A | 3/1993 | Guckel | 205/118 |
| 5,226,909 A | 7/1993 | Evans et al. | |
| 5,284,486 A | 2/1994 | Kotula et al. | |
| 5,378,583 A | 1/1995 | Guckel et al. | |
| 5,411,511 A | 5/1995 | Hall | |
| 5,465,444 A | 11/1995 | Bigler et al. | |
| 5,484,112 A | 1/1996 | Koenig | 241/236 |
| 5,496,668 A | 3/1996 | Guckel et al. | |
| 5,522,829 A | 6/1996 | Michalos | |
| 5,576,147 A | 11/1996 | Guckel et al. | |
| 5,591,187 A | 1/1997 | Dekel | |
| 5,601,556 A | 2/1997 | Pisharodi | |
| 5,618,293 A | 4/1997 | Sample et al. | |
| 5,643,304 A | 7/1997 | Schechter et al. | |
| 5,662,284 A | 9/1997 | Koenig | 241/236 |
| 5,685,838 A | 11/1997 | Peters et al. | |
| 5,695,510 A * | 12/1997 | Hood | 606/169 |
| 5,718,618 A | 2/1998 | Guckel et al. | |
| 5,725,530 A * | 3/1998 | Popken | 606/82 |
| 5,782,848 A | 7/1998 | Lennox | |
| 5,788,169 A | 8/1998 | Koenig | 241/236 |
| 5,823,990 A | 10/1998 | Henley | |
| 5,846,244 A * | 12/1998 | Cripe | 606/82 |
| 5,866,281 A | 2/1999 | Guckel et al. | |
| 5,908,719 A | 6/1999 | Guckel et al. | |
| 5,910,150 A * | 6/1999 | Saadat | 606/159 |
| 5,916,231 A | 6/1999 | Bays | |
| 5,928,158 A | 7/1999 | Aristides | |
| 5,928,161 A | 7/1999 | Krulevitch et al. | |
| 5,957,881 A | 9/1999 | Peters et al. | |
| 6,001,112 A | 12/1999 | Taylor | |
| 6,010,477 A | 1/2000 | Bays | |
| 6,013,991 A | 1/2000 | Philipp | |
| 6,027,630 A | 2/2000 | Cohen | 205/135 |
| 6,063,088 A | 5/2000 | Winslow | |
| 6,221,088 B1 | 4/2001 | Bays | |
| 6,293,957 B1 | 9/2001 | Peters et al. | |
| 6,447,525 B2 | 9/2002 | Follmer et al. | |
| 6,475,369 B1 | 11/2002 | Cohen | |
| 6,517,544 B1 | 2/2003 | Michelson | |
| 6,565,588 B1 | 5/2003 | Clement et al. | |
| 6,572,742 B1 | 6/2003 | Cohen | |
| 6,613,972 B2 | 9/2003 | Cohen et al. | |
| 6,666,874 B2 | 12/2003 | Heitzmann et al. | |
| 6,761,723 B2 | 7/2004 | Buttermann et al. | |
| 6,790,377 B1 | 9/2004 | Cohen | |
| 6,951,456 B2 | 10/2005 | Cohen et al. | |
| 7,160,304 B2 | 1/2007 | Michelson | |
| 7,163,614 B2 | 1/2007 | Cohen | |
| 7,195,989 B2 | 3/2007 | Lockard et al. | |
| 7,229,544 B2 | 6/2007 | Cohen | |
| 7,235,088 B2 | 6/2007 | Pinto et al. | |
| 7,239,219 B2 | 7/2007 | Brown et al. | |
| 7,252,861 B2 | 8/2007 | Smalley | |
| 7,479,147 B2 | 1/2009 | Honeycutt et al. | |
| 7,699,790 B2 | 4/2010 | Simpson | |
| 2003/0130662 A1 | 7/2003 | Michelson | 606/79 |
| 2004/0138672 A1 | 7/2004 | Michelson | |
| 2005/0021065 A1 | 1/2005 | Yamada et al. | |
| 2005/0029109 A1 | 2/2005 | Zhang et al. | |
| 2005/0059905 A1 | 3/2005 | Boock et al. | |
| 2005/0222598 A1 | 10/2005 | Ho et al. | |
| 2006/0184175 A1 | 8/2006 | Schomer et al. | |
| 2006/0200152 A1 | 9/2006 | Karubian et al. | |
| 2006/0212060 A1 | 9/2006 | Hacker et al. | |
| 2006/0217730 A1 | 9/2006 | Termanini | |
| 2006/0229646 A1 | 10/2006 | Sparks | |
| 2006/0241566 A1 | 10/2006 | Moon et al. | 604/540 |
| 2006/0282065 A1 | 12/2006 | Cohen | |
| 2007/0073303 A1 * | 3/2007 | Namba | 606/82 |
| 2007/0100361 A1 * | 5/2007 | Cohen | 606/167 |
| 2007/0197895 A1 | 8/2007 | Nycz et al. | |
| 2007/0198038 A1 | 8/2007 | Cohen et al. | |
| 2007/0219459 A1 | 9/2007 | Cohen | |
| 2007/0260253 A1 | 11/2007 | Johnson et al. | 606/79 |
| 2007/0265648 A1 | 11/2007 | Cohen | |
| 2008/0004643 A1 | 1/2008 | To et al. | |
| 2008/0161809 A1 | 7/2008 | Schmitz et al. | |
| 2008/0249553 A1 | 10/2008 | Gruber et al. | |
| 2009/0012524 A1 | 1/2009 | Dower | |
| 2009/0018565 A1 | 1/2009 | To et al. | |
| 2010/0010492 A1 | 1/2010 | Lockard et al. | |
| 2010/0010525 A1 | 1/2010 | Lockard et al. | |

OTHER PUBLICATIONS

Schmitz et al.; U.S. Appl. No. 13/289,994 entitled "Selective Tissue Removal Tool for Use in Medical Applications and Methods for Making and Using," filed Nov. 4, 2011.

Cohen, et al., "EFAB: Batch Production of Functional, Fully-Dense Metal Parts with Micron-Scale Features", Proc. 9th Solid Freeform Fabrication, The University of Texas at Austin, Aug. 1998, pp. 161.

Adam L. Cohen, et al., "EFAB: Rapid, Low-Cost Desktop Micromachining of High Aspect Ratio True 3-D MEMS", Proc. 12th IEEE Micro Electro Mechanical Systems Workshop, IEEE, Jan. 17-21, 1999, pp. 244-251.

"Microfabrication—Rapid Prototyping's Killer Application", Rapid Prototyping Report, CAD/CAM Publishing, Inc., Jun. 1999, pp. 1-5.

Adam L. Cohen, "3-D Micromachining by Electrochemical Fabrication", Micromachine Devices, Mar. 1999, pp. 6-7.

Gang Zhang, et al., "EFAB: Rapid Desktop Manufacturing of True 3-D Microstructures", Proc. 2nd International Conference on Integrated MicroNanotechnology for Space Applications, The Aerospace Co., Apr. 1999.

F. Tseng, et al., "EFAB: High Aspect Ratio, Arbitrary 3-D Metal Microstructures Using a Low-Cost Automated Batch Process", 3rd International Workshop on High Aspect Ratio Microstructure Technology (HARMST'99), Jun. 1999.

Adam L. Cohen, et al., "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, Sep. 1999.

F. Tseng, et al., "EFAB: High Aspect Ratio, Arbitrary 3-D Metal Microstructures Using a Low-Cost Automated Batch Process", MEMS Symposium, ASME 1999 International Mechanical Engineering Congress and Exposition, Nov. 1999.

Adam L. Cohen, "Electrochemical Fabrication (EFABTM)", Chapter 19 of the MEMS Handbook, edited by Mohamed Gad-El-Hak, CRC Press, 2002, pp. 19/1-19/23.

SSI Shredding Systems, www.ssiworld.com, Sep. 24, 2009.

Chen et al.; U.S. Appl. No. 13/388,653 entitled "Concentric Cutting Devices for Use in Minimally Invasive Medical Procedures." filed Apr. 16, 2012.

* cited by examiner

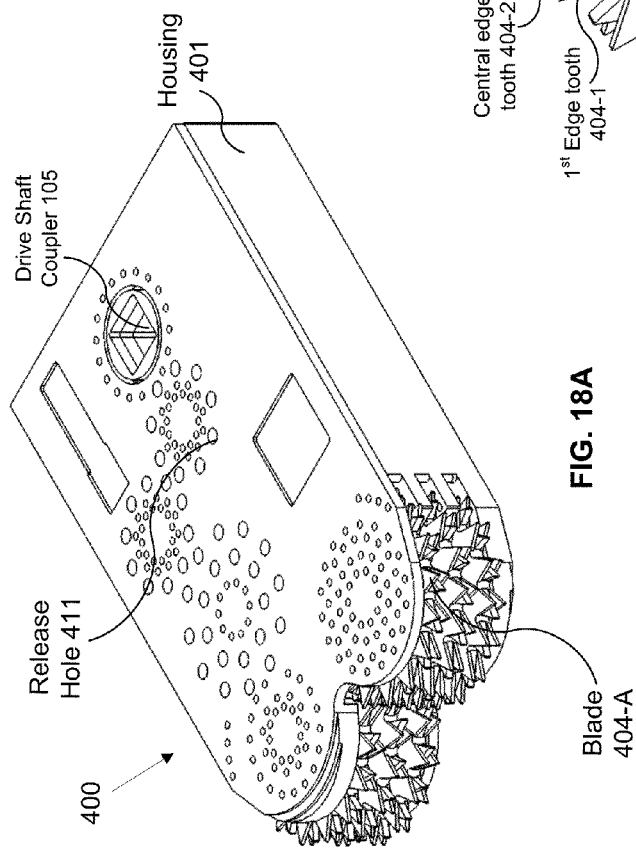
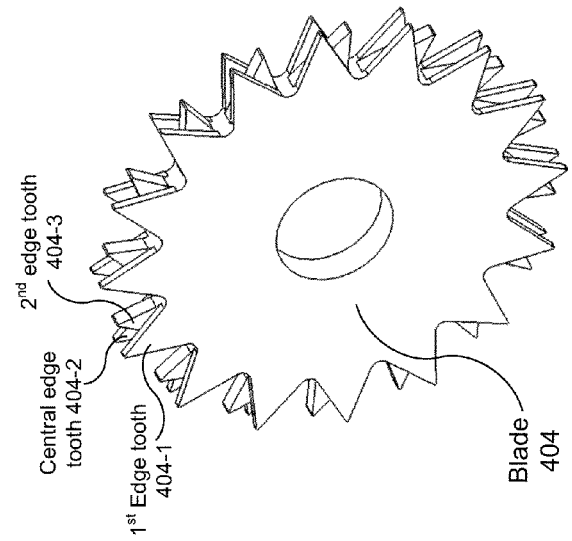
FIG. 18A
FIG. 18B

MINIATURE SHREDDING TOOL FOR USE IN MEDICAL APPLICATIONS AND METHODS FOR MAKING

RELATED APPLICATIONS

This application claims benefit of U.S. Provisional Patent Application No. 61/075,007 filed Jun. 24, 2008 and is a continuation-in-part of U.S. patent application Ser. No. 12/490,295 filed Jun. 23, 2009; the '295 application in turn claims benefit of U.S. Provisional Application Nos. 61/075,006, filed Jun. 23, 2008; 61/164,864, filed Mar. 30, 2009; and 61/164,883, filed Mar. 30, 2009. Each of these applications is incorporated herein by reference as if set forth in full herein.

U.S. GOVERNMENT RIGHTS

At least a portions of the inventions disclosed and claimed herein were made with government support under Grant No. R01 HL087797 awarded by the National Institute of Health. The Government has certain rights in these inventions.

FIELD OF THE INVENTION

Embodiments of the present invention relate to micro-scale and millimeter-scale shredding devices that may, for example, be used to remove unwanted tissue or other material from selected locations within a body of a patient during a surgical or other medical procedure (e.g. a percutaneous or minimally invasive procedure) while other embodiments are related to such procedures and still others are related to making such devices using multi-layer, multi-material electrochemical fabrication methods.

BACKGROUND OF THE INVENTION

1. Electrochemical Fabrication

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allow the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING™ or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p 161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p 244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-El-Hak, CRC Press, 2002.

(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.

2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.

3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i.e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

2. Applications and Uses

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within these various fields to produce new structures, certain uses for Electrochemical Fabrication provide designs, structures, capabilities and/or features not known or obvious in view of the states of the art in these various fields.

SUMMARY OF THE INVENTION

It is an object of some embodiments of the invention to provide an improved micro-scale or millimeter scale shredding device for use in medical procedures.

It is an object of some embodiments of the invention to provide an improved micro-scale or millimeter scale shredding device for use in medical procedures with (1) improved positional stabilization while operating in a working region, (2) improved blades for disrupting or shredding a material that is to be removed; and/or (3) reduced unintended outflow of shredded material from the shredding device back into the working region outside of the shredding device.

It is an object of some embodiments of the invention to provide improved medical procedures (e.g. minimally invasive procedures) for removing tissue or other material from the body of a patient.

It is an object of some embodiments of the invention to provide an improved medical procedures (e.g. minimally invasive procedures) involving use of a microscale or millimeter scale shredding device having (1) improved positional stabilization while operating in a working region, (2) improved blades for disrupting or shredding a material that is to be removed; and/or (3) reduced unintended outflow of shredded material from the shredding device back into the working region outside of the shredding device.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

A first aspect of the invention provides a microscale or millimeter scale shredding tool for use in a medical procedure, including: (a) a housing having a distal end and a proximal end; (b) a first multi-blade blade stack mounted for rotational motion about a first axis relative to the housing and extending in part from the housing; (c) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset in the direction of the first and second axes so that the blades of first stack do not interfere with the blade of the second stack; and (d) a drive mechanism for rotating the blades of the first stack and the blades of the second stack in opposite directions; wherein at least one of the blades of the first or second multi-blade stack comprises a first and second side and a plurality of cutting tips wherein the maximum radial extension of the at least some of the tips are located on the first side of the blade while the maximum radial extension of the at least some other tips are located on the second side of the blade, and wherein the shredding tool provides for intake and shredding of material encountered during the medical procedure.

Numerous variations of the first aspect of the invention exist and include for example: at least some of the tips alternating around a circumference of the blade with the at least some other tips.

A second aspect of the invention provides a microscale or millimeter scale shredding tool for use in a medical procedure, including: (a) housing having a distal end and a proximal end; (b) a first multi-blade blade stack mounted for rotational motion about a first axis relative to the housing and extending in part from the housing; (c) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (d) a drive mechanism for rotating the blades of the first stack and the blades of the second stack in opposite directions; wherein the housing includes shrouds that result in the first and second blades stacks being shielded around at least one half of their periphery to provide for reduced outflow of shredded material than if the shielding extended around less than one half their periphery.

A third aspect of the invention provides a microscale or millimeter scale shredding tool for use in a medical application, including: (a) a housing having a distal end and a proximal end; (b) a first multi-blade blade stack mounted for rotational motion about a first axis relative to the housing and extending in part from the housing; (c) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (d) a drive mechanism for rotating the blades of the first stack and the blades of the second stack in opposite directions; wherein at least one position stabilizing mechanism extends from housing so to interact with tissue within a body of a patient to stabilize the position of the tool during shredding operations, wherein the shredding tool provides for intake and shredding of material encountered during the medical procedure.

Numerous variations of the third aspect of the invention exist and include for example: (1) the stabilizing mechanism comprises a spike and (2) the spike comprises a plurality of spikes.

Another variation of the first-third aspects of the invention include: (i) the first multi-blade blade stack comprising a plurality of first circular blades with first cutting elements extending from circumferences of the first circular blades, (ii) the second multi-blade blade stack comprising a plurality of second circular blades with second cutting elements extending from circumferences of the second circular blades, (iii) each of the first circular blades rotating about a first common axis, (iv) each of the first circular blades rotating about a second common axis, (v) the first circular blades each having a first thickness and a first gap relative to an immediate neighboring first circular blade, (vi) the second circular blades each having a second thickness and a second gap relative to an immediate neighboring second circular blade, and (vii) the first thickness relative to the second gap and the second thickness relative to the first gap allowing interlacing and movement of the first and second blades while providing for intake and shredding of material encountered by the blades during the medical procedure.

Additional variations of the first-third aspects of the invention and their variations, include, for example: (1) The tools, at least in part, being formed from a plurality of stacked layers of deposited material wherein the deposited material may be electrodeposited material; (2) the procedure is a minimally invasive procedure; and/or (3) the material being tissue.

A fourth aspect of the invention provides a microscale or millimeter scale shredding tool for use in a medical procedure, including (a) a housing having a distal end and a proximal end; (b) a first multi-blade blade stack mounted for rotational motion about a first axis relative to the housing and extending in part from the housing; and (c) a drive mechanism for rotating the blades of the first stack; wherein at least one of the blades of the first stack comprises a first and second side and a plurality of cutting tips wherein the maximum radial extension of the at least some of the tips are located on the first side of the blade while the maximum radial extension of the at least some other tips are located on the second side of the blade, wherein the shredding tool provides for intake and shredding of material encountered during the medical procedure.

A first variation of the fourth aspect of the invention additionally provides: (d) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset in the direction of the first and second axes so that the blades of first stack do not interfere with the blade of the second stack; and (e) a drive mechanism for rotating the blades of the second stack in an opposite direction relative to the rotation of the blades of the first stack.

Another variation of the fourth aspect of the invention includes at least some of the tips alternate around a circumference of the blade with the at least some other tips.

A fifth aspect of the invention provides a microscale or millimeter scale shredding tool for use in a medical procedure, including: (a) a housing having a distal end and a proximal end; (b) a first multi-blade blade stack mounted for rotational motion about a first axis relative to the housing and extending in part from the housing; wherein the housing includes a shroud that result in the first blade stacks being shielded around at least one half of its periphery to provide for reduced outflow of shredded material than if the shielding extended around less than one half their periphery, wherein the shredding tool provides for intake and shredding of material encountered during the medical procedure.

A first variation of the fifth aspect of the invention additionally provides: (c) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (d) a drive mechanism for rotating the blades of the second stack in an opposite direction to that of the rotation of the blades of the first stack; wherein the shroud includes a plurality of shrouds that result in the first and second blades stacks being shielded around at least one half of their periphery to provide for reduced outflow of shredded material than if the shielding extended around less than one half their periphery.

A sixth aspect of the invention provides, a microscale or millimeter-scale shredding tool for use in a medical application, including: (a) a housing having a distal end and a proximal end; (b) a first multi-blade blade stack mounted for rotational motion about a first axis relative to the housing and extending in part from the housing; and (c) a drive mechanism for rotating the blades of the first stack; wherein at least one position stabilizing mechanism extends from housing so to interact with tissue within a body of a patient to stabilize the position of the tool during shredding operations, wherein the shredding tool provides for intake and shredding of material encountered during the medical procedure.

A first variation of the sixth aspect of the invention provides: (d) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (e) a drive mechanism for rotating the blades of the second stack in an opposite direction relative to the rotation of the first stack of blades;

Further example variations of the sixth aspect of the invention include the stabilizing mechanism comprising a spike, and possibly the spike comprising a plurality of spikes.

Another variation of the first variations of the fourth-sixth aspects of the invention include: (i) the first multi-blade blade stack comprising a plurality of first circular blades with first cutting elements extending from circumferences of the first circular blades, (ii) the second multi-blade blade stack comprising a plurality of second circular blades with second cutting elements extending from circumferences of the second circular blades, (iii) each of the first circular blades rotating about a first common axis, (iv) each of the first circular blades rotating about a second common axis, (v) the first circular blades each having a first thickness and a first gap relative to an immediate neighboring first circular blade, (vi) the second circular blades each having a second thickness and a second gap relative to an immediate neighboring second circular blade, and (vii) the first thickness relative to the second gap and the second thickness relative to the first gap allowing interlacing and movement of the first and second blades while providing for intake and shredding of material encountered by the blades during the medical procedure.

Additional variations of the fourth-sixth aspects of the invention and their variations, include, for example: (1) The tools, at least in part, being formed from a plurality of stacked layers of deposited material wherein the deposited material may be electrodeposited material; (2) the procedure is a minimally invasive procedure; and/or (3) the material being tissue.

A seventh aspect of the invention provides a medical procedure including: (a) insertion of a microscale or millimeter scale shredding tool into a working area with a body of a patient, comprising: (i) a housing having a distal end and a proximal end; (ii) a first multi-blade blade stack mounted for rotational motion about a first axis relative to the housing and extending in part from the housing, wherein at least one of the blades of the first stack comprises a first and second side and a plurality of cutting tips wherein the maximum radial extension of the at least some of the tips are located on the first side of the blade while the maximum radial extension of the at least some other tips are located on the second side of the blade, and (iii) a drive mechanism for rotating the blades of the first stack; and (b) powering the drive mechanism and moving the shredding tool to desired locations within the working area to intake and shred selected material; and (c) extracting the shredding tool from the working area and from the body of the patient.

A first variation of the seventh aspect of the invention adds the following features to the tool: (d) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset in the direction of the first and second axes so that the blades of first stack do not interfere with the blade of the second stack; and (e) a drive mechanism for rotating the blades of the second stack in an opposite direction relative to the rotation of the blades of the first stack;

A second variation of the seventh aspect of the invention provides for at least some of the tips of the tool alternating around a circumference of the blade with the at least some other tips.

An eighth aspect of the invention provides a medical procedure including: (a) insertion of a microscale or millimeter scale shredding tool into a working area with a body of a patient, comprising: (i) a housing having a distal end and a proximal end; and (ii) a first multi-blade blade stack mounted for rotational motion about a first axis relative to the housing and extending in part from the housing, wherein the housing includes a shroud that result in the first blade stacks being shielded around at least one half of its periphery to provide for reduced outflow of shredded material than if the shielding extended around less than one half their periphery, (b) powering on the drive mechanism and moving the shredding tool to desired locations within the working area to intake and shred selected material; and (c) extracting the shredding tool from the working area and from the body of the patient.

A first variation of the eighth aspect of the invention adds the following features to the tool: (iii) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (iv) a drive mechanism for rotating the blades of the second stack in an opposite direction to that of the rotation of the blades of the first stack; and wherein the shroud includes a plurality of shrouds that result in the first and second blades stacks being shielded around at least one half of their periphery to provide for reduced outflow of shredded material than if the shielding extended around less than one half their periphery.

A ninth aspect of the invention provides a medical procedure including: (a) insertion of a microscale or millimeter scale shredding tool into a working area with a body of a patient, comprising: (i) housing having a distal end and a proximal end wherein at least one position stabilizing mechanism extends from housing so to interact with tissue within a body of a patient to stabilize the position of the tool during shredding operations; (ii) a first multi-blade blade stack mounted for rotational motion about a first axis relative to the housing and extending in part from the housing; (iii) a drive mechanism for rotating the blades of the first stack; (b) powering on the drive mechanism and moving the shredding tool to desired locations within the working area to intake and shred selected material; and (c) extracting the shredding tool from the working area and from the body of the patient.

A first variation of the ninth aspect of the invention adds the following features to the tool (iv) a second multi-blade blade stack mounted for rotational motion, about a second axis which is parallel to the first axis, relative to the housing and extending in part from the housing, wherein a least a portion of the blades of the second blade stack have interlaced positions with blades of the first stack in a plane perpendicular to the first and second axes of rotation but which are offset along in the direction of the first and second axis so that the blades of first stack do not interfere with the blade of the second stack; and (v) a drive mechanism for rotating the blades of the second stack in an opposite direction relative to the rotation of the first stack of blades.

Additional variations of the ninth aspect of the invention provide for the stabilizing mechanism to include a spike and possible the spike to include a plurality of spikes.

Another variation of the first variations of the seventh-ninth aspects of the invention provide: (i) the first multi-blade blade stack comprising a plurality of first circular blades with first cutting elements extending from circumferences of the first circular blades, (ii) the second multi-blade blade stack comprising a plurality of second circular blades with second cutting elements extending from circumferences of the second circular blades, (iii) each of the first circular blades rotating about a first common axis, (iv) each of the first circular blades rotating about a second common axis, (v) the first circular blades each having a first thickness and a first gap relative to an immediate neighboring first circular blade, (vi) the second circular blades each having a second thickness and a second gap relative to an immediate neighboring second circular blade, and (vii) the first thickness relative to the second gap and the second thickness relative to the first gap allowing interlacing and movement of the first and second blades while providing for intake and shredding of material encountered by the blades during the medical procedure.

Additional variations of the seventh-ninth aspects of the invention and their variations, include, for example: (1) The tools, at least in part, being formed from a plurality of stacked layers of deposited material wherein the deposited material may be electrodeposited material; (2) the procedure is a minimally invasive procedure; and/or (3) the material being tissue.

The disclosure of the present invention provides a number of device embodiments which may be formed from a plurality of formed and adhered layers with each successive layer including at least two materials, one of which is a structural material and the other of which is a sacrificial material, and wherein each successive layer defines a successive cross-section of the three-dimensional structure, and wherein the forming of each of the plurality of successive layers includes: (i) depositing a first of the at least two materials; (ii) depositing a second of the at least two materials; and (B) after the forming of the plurality of successive layers, separating at least a portion of the sacrificial material from the structural material to reveal the three-dimensional structure. In some embodiments, the device may include a plurality of components movable relative to one another which contain etching holes which may be aligned during fabrication and during release from at least a portion of the sacrificial material.

Other aspects of the invention will be understood by those of skill in the art upon review of the teachings herein. Other aspects of the invention may involve combinations of the above noted aspects of the invention. Other aspects of the invention may involve apparatus that can be used in implementing one or more of the above method aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 18A and 18B provide perspective views of a device according to a fourth embodiment of the invention and of a blade of that device which distinguishes the device from the device of the first embodiment wherein each blade is made from three levels of structure (e.g. layers) wherein the blades may be considered hybrid blades wherein the second level is shifted to place the phase of its teeth ahead of those of the first and third levels where the shift in phase is less than ½ the distance between consecutive teeth.

DETAILED DESCRIPTION OF PREFERRED EMBODIMENTS

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 1A:
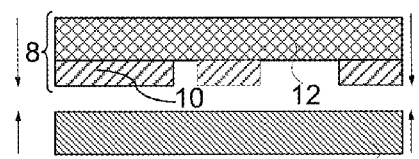
FIGS. 1A-1C schematically depict side views of various stages of a CC mask plating process, while FIGS. 1D-G schematically depict a side views of various stages of a CC mask plating process using a different type of CC mask.
Figure 1B:
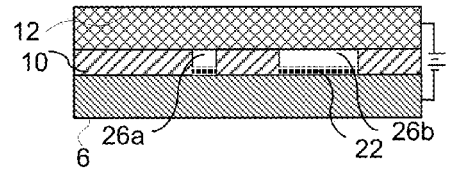
Figure 1C:
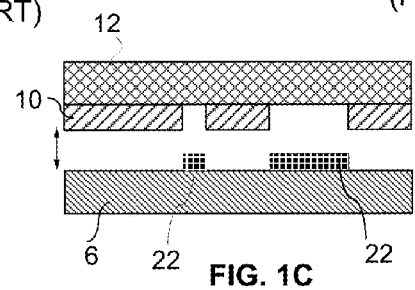
Figure 1D:
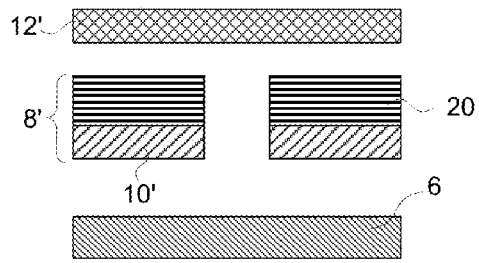
Figure 1E:
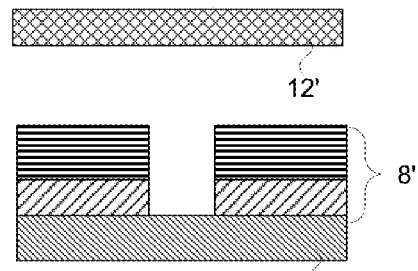
Figure 1F:
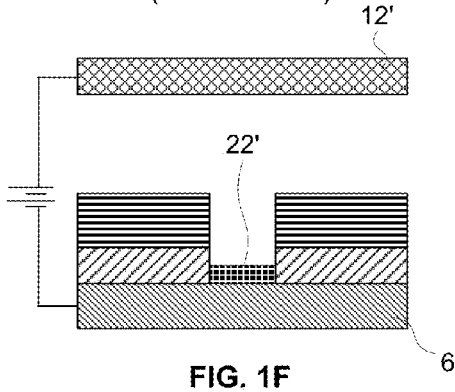
Figure 1G:
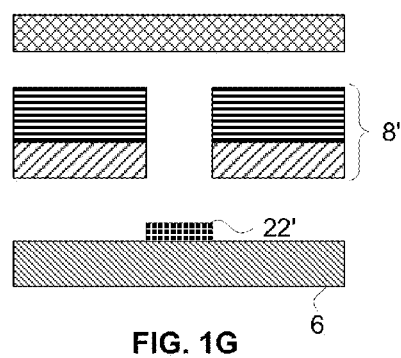
Figure 2A:
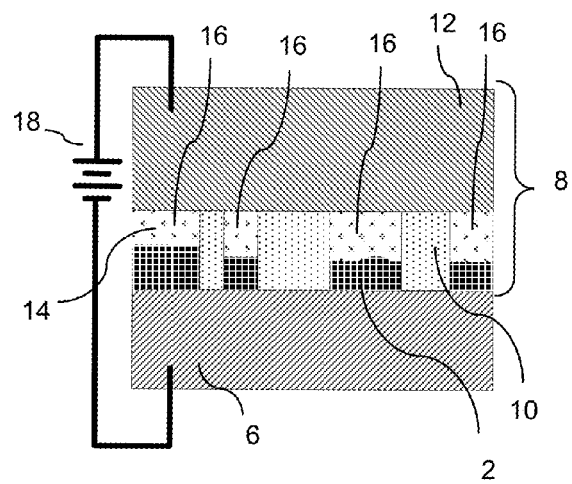
FIGS. 2A-2F schematically depict side views of various stages of an electrochemical fabrication process as applied to the formation of a particular structure where a sacrificial material is selectively deposited while a structural material is blanket deposited.
Figure 2B:
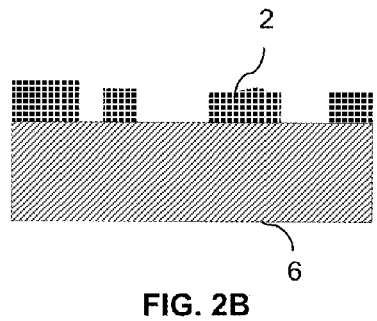
Figure 2C:
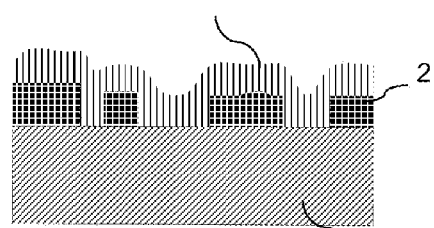
Figure 2D:
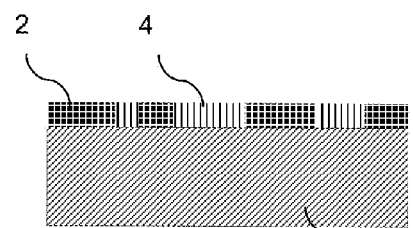
Figure 2E:
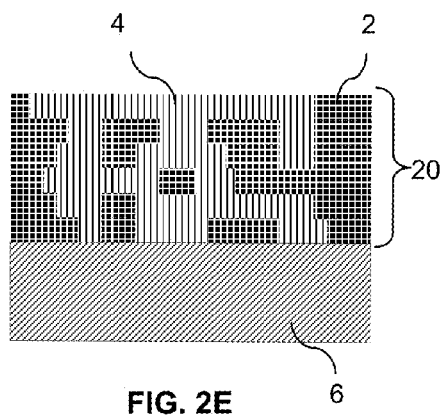
Figure 2F:
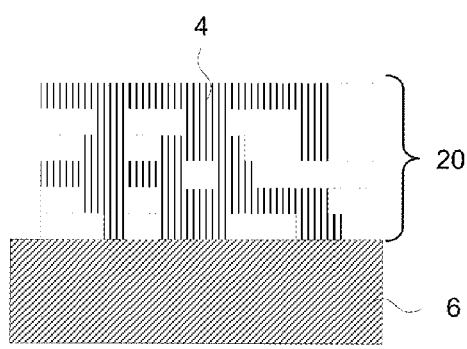
Figure 3A:
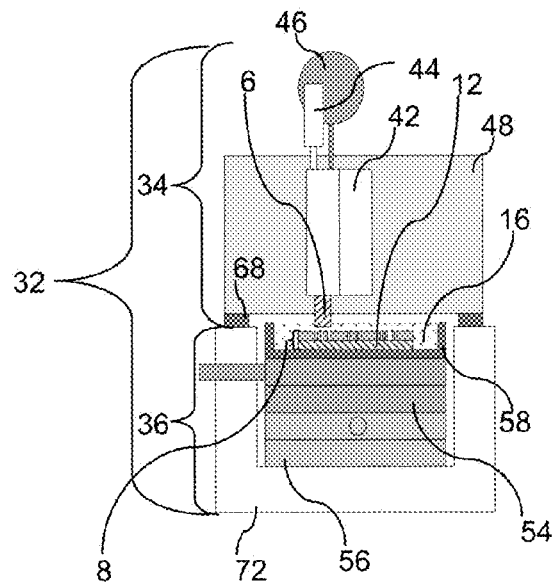
FIGS. 3A-3C schematically depict side views of various example subassemblies that may be used in manually implementing the electrochemical fabrication method depicted in FIGS. 2A-2F.
Figure 3B:
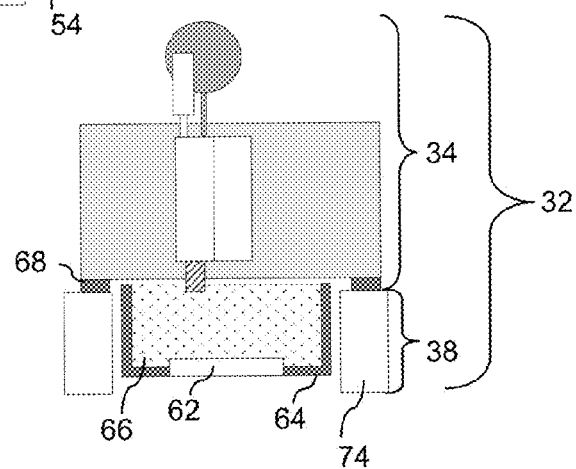
Figure 3C:
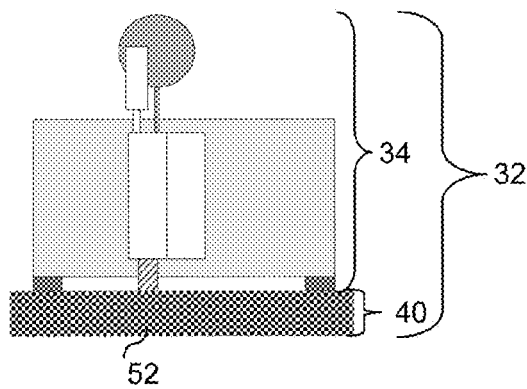
Figure 4A:
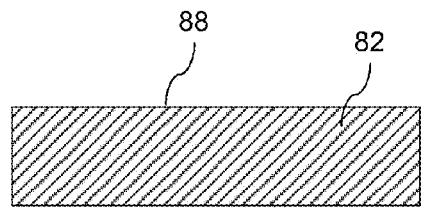
FIGS. 4A-4F schematically depict the formation of a first layer of a structure using adhered mask plating where the blanket deposition of a second material overlays both the openings between deposition locations of a first material and the first material itself
Figure 4B:
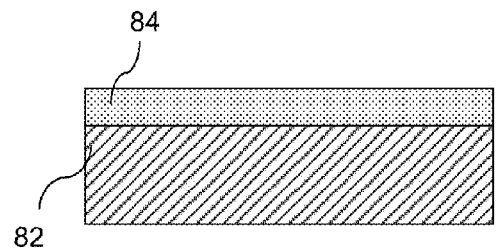
Figure 4C:
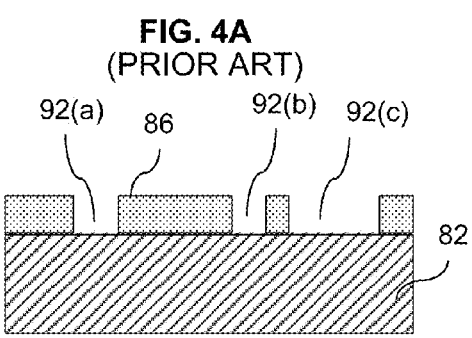
Figure 4D:
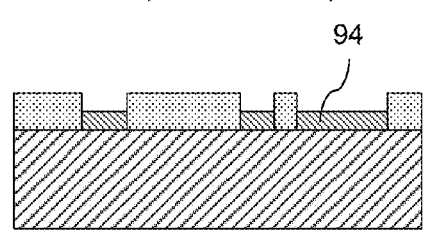
Figure 4E:
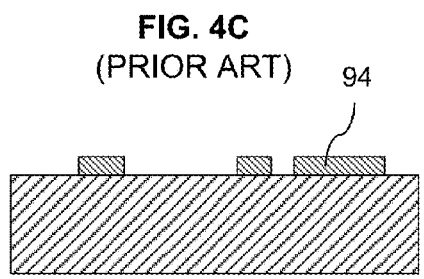
Figure 4F:
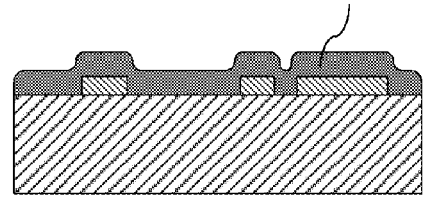
Figure 4G:
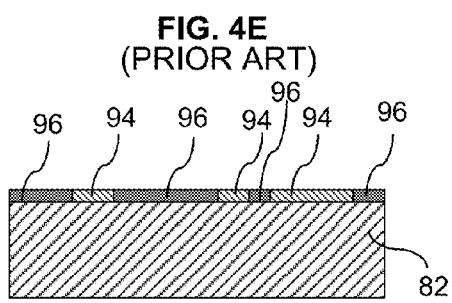
FIG. 4G depicts the completion of formation of the first layer resulting from planarizing the deposited materials to a desired level.
Figure 4H:
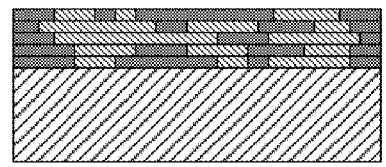
FIGS. 4H and 4I respectively depict the state of the process after formation of the multiple layers of the structure and after release of the structure from the sacrificial material.
Figure 4I:
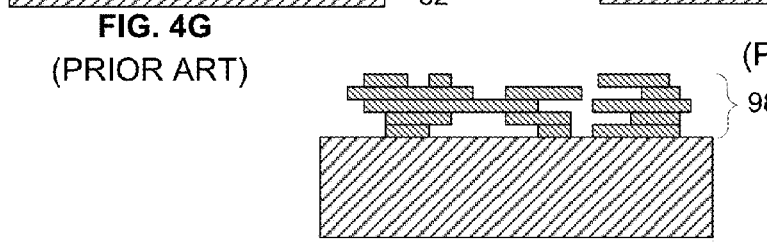

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4 G several times to form a multi-layer structure are shown where each layer consists of two materials. For most applications, one of these materials is removed as shown in FIG. 4I to yield a desired 3-D structure 98 (e.g. component or device).

Various embodiments of various aspects of the invention are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable. In the present application meso-scale and millimeter scale have the same meaning and refer to devices that may have one or more dimensions extending into the 0.5-20 millimeter range, or somewhat larger and with features positioned with precision in the 10-100 micron range and with minimum features sizes on the order of 100 microns.

The various embodiments, alternatives, and techniques disclosed herein may form multi-layer structures using a single patterning technique on all layers or using different patterning techniques on different layers. For example, various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. patent application Ser. No. 10/434,519, by Smalley, now U.S. Pat. No. 7,252,861, and entitled "Methods of and Apparatus for Electrochemically Fabricating Structures Via Interlaced Layers or Via Selective Etching and Filling of Voids layer elements" which is hereby incorporated herein by reference as if set forth in full.

Temporary substrates on which structures may be formed may be of the sacrificial-type (i.e. destroyed or damaged during separation of deposited materials to the extent they can not be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

DEFINITIONS

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519, now U.S. Pat. No. 7,252,861. This referenced application is incorporated herein by reference as if set forth in full. In most embodiments, a build layer includes at least one primary structural material and at least one primary sacrificial material. However, in some embodiments, two or more primary structural materials may used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization may be followed or proceeded by thermally induced planarization (.e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, barrier layer materials (e.g. diffusion barrier material), and the like. These secondary structural materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. In other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 $\mu m^2$) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 20% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "n".

"Minimum feature size" refers to a necessary or desirable spacing between structural material elements on a given layer that are to remain distinct in the final device configuration. If the minimum feature size is not maintained on a given layer, the fabrication process may result in structural material inadvertently bridging the two structural elements due to masking material failure or failure to appropriately fill voids with sacrificial material during formation of the given layer such that during formation of a subsequent layer structural material inadvertently fills the void. More care during fabrication can lead to a reduction in minimum feature size or a willingness to accept greater losses in productivity can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of sacrificial material regions. Conversely a minimum feature size for structure material regions (minimum width or length of structural material elements) may be specified. Depending on the fabrication method and order of deposition of structural material and sacrificial material, the two types of minimum feature sizes may be different. In practice, for example, using electrochemical fabrication methods and described herein, the minimum features size on a given layer may be roughly set to a value that approximates the layer thickness used to form the layer and it may be considered the same for both structural and sacrificial material widths and lengths. In some more rigorously implemented processes, examination regiments, and rework requirements, it may be set to an amount that is 80%, 50%, or even 30% of the layer thickness. Other values or methods of setting minimum feature sizes may be set.

"Sublayer" as used herein refers to a portion of a build layer that typically includes the full lateral extents of that build layer but only a portion of its height. A sublayer is usually a vertical portion of build layer that undergoes independent processing compared to another sublayer of that build layer.

A Shredding Device According to First-Fourth Embodiments of the Invention

Figure 10:
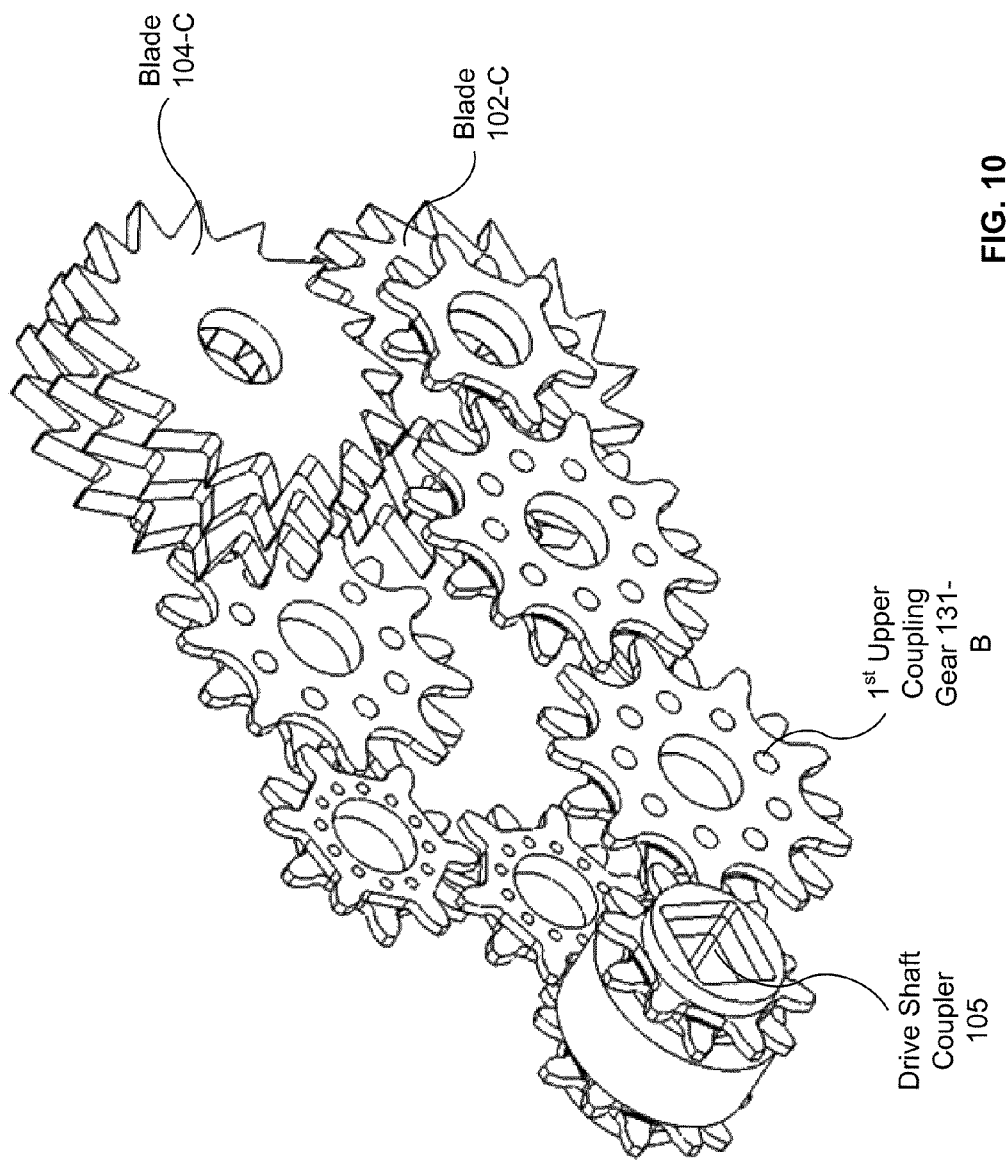
FIG. 10 provides an alternative perspective side view of the gear train of the device of the first embodiment.
Figure 11:
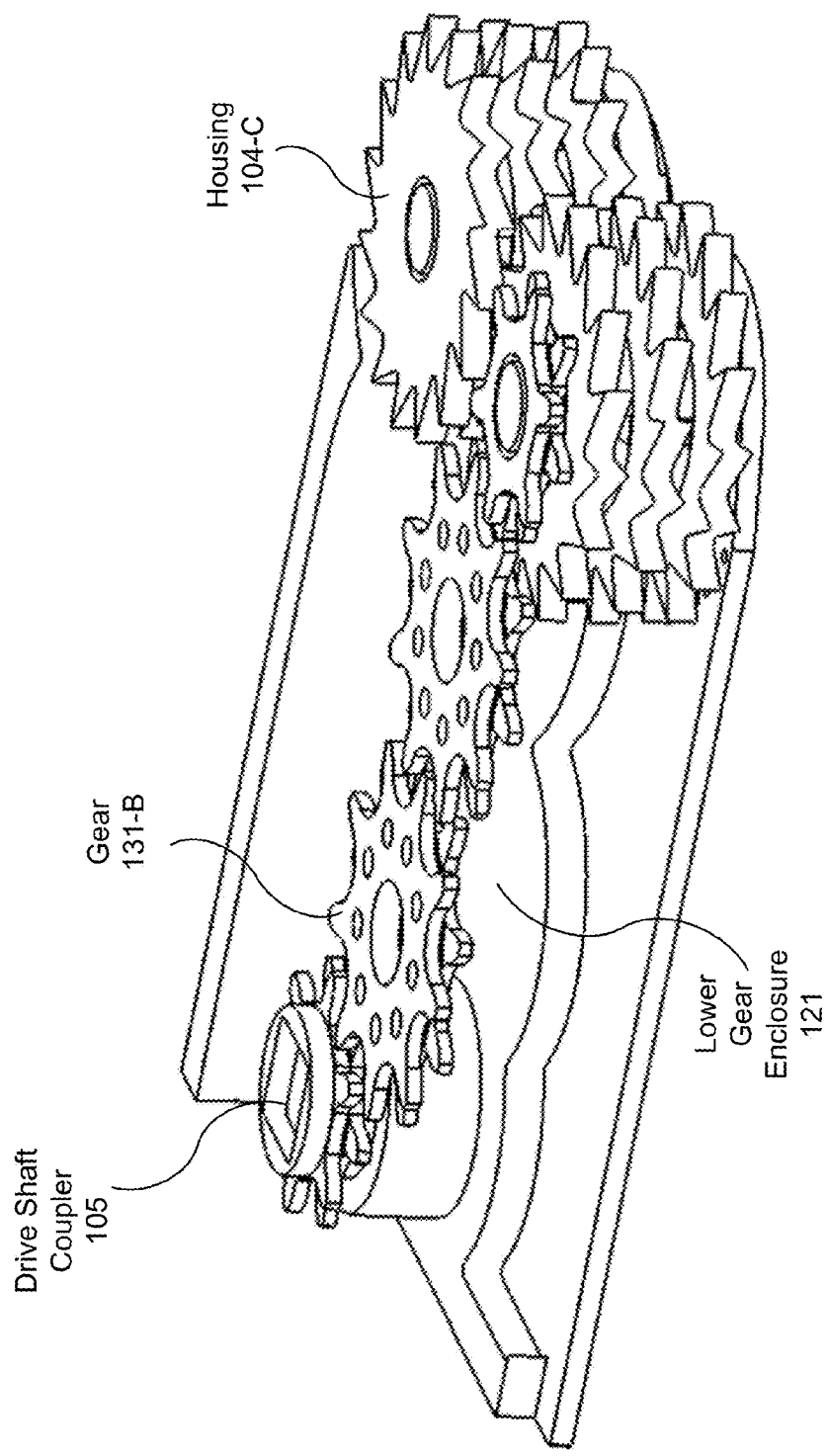
FIG. 11 provides a perspective side view of the upper gear train of the device of the first embodiment along with an enclosure that shields the lower gear train from an interior cavity of the device wherein an upper portion of the outer housing is removed to enable viewing of the gear train.
Figure 12:
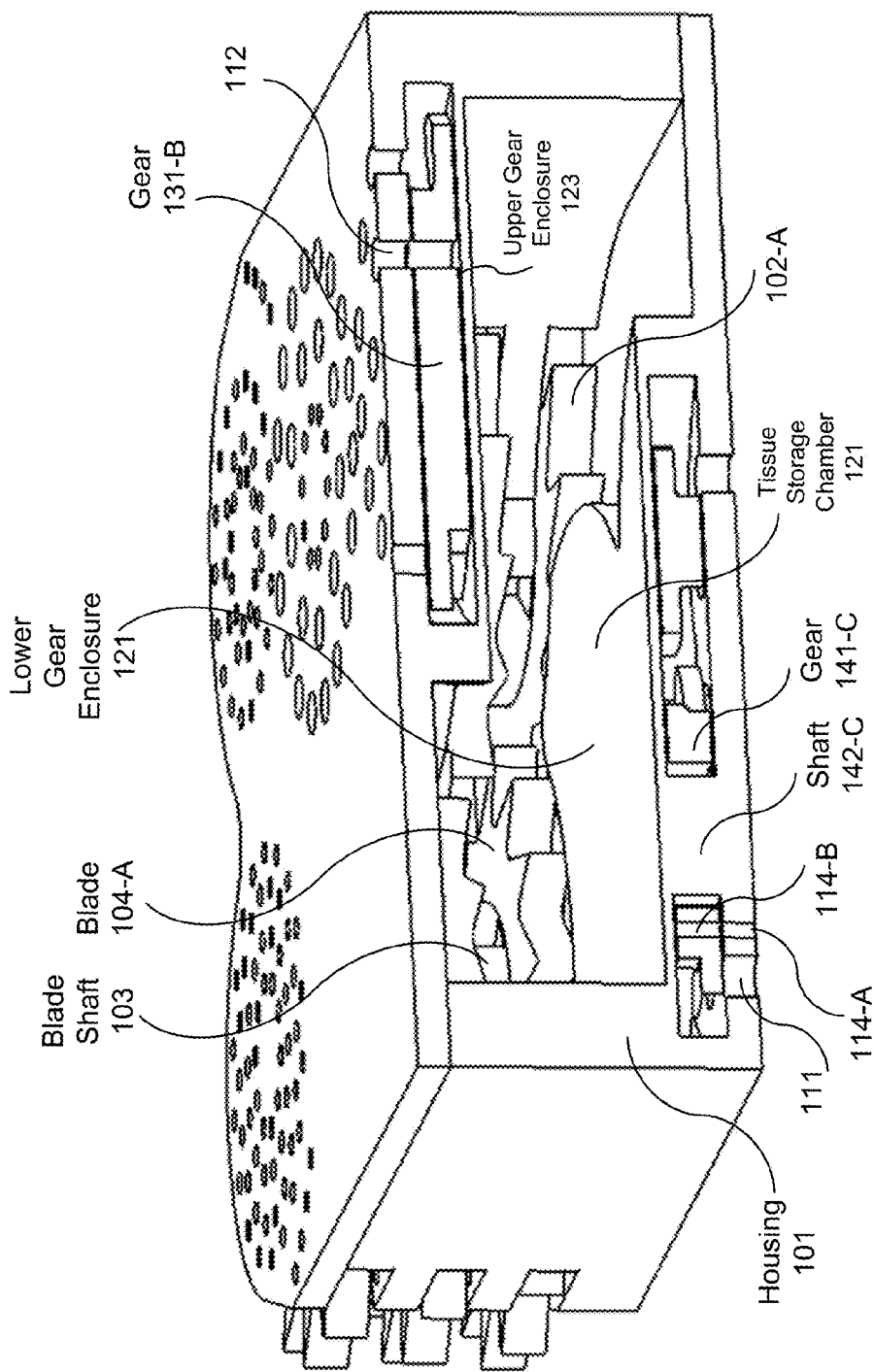
FIG. 12 provides a perspective cross-sectional view of the rear portion of the device of the first embodiment with the back shielding and a portion of the gears cut away so that the relationship between the gears, the upper and lower gear enclosures, and outer housing of the device can be seen.
Figure 13:
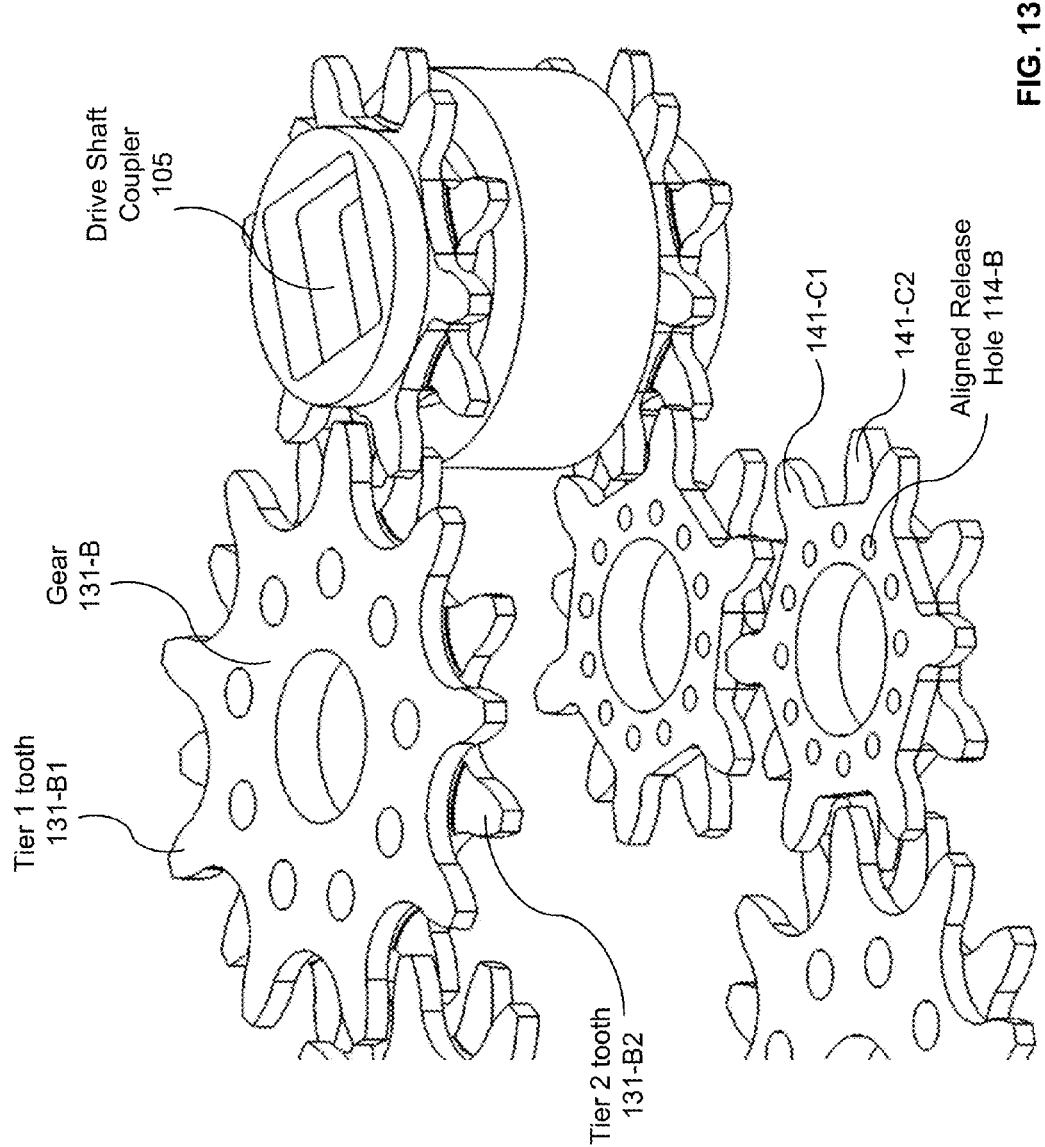
FIG. 13 provides a close up perspective view of the proximal gears in the drive chain and the drive coupler (that couples rotational force with the upper and lower drive chain) of the first embodiment.
Figure 14:
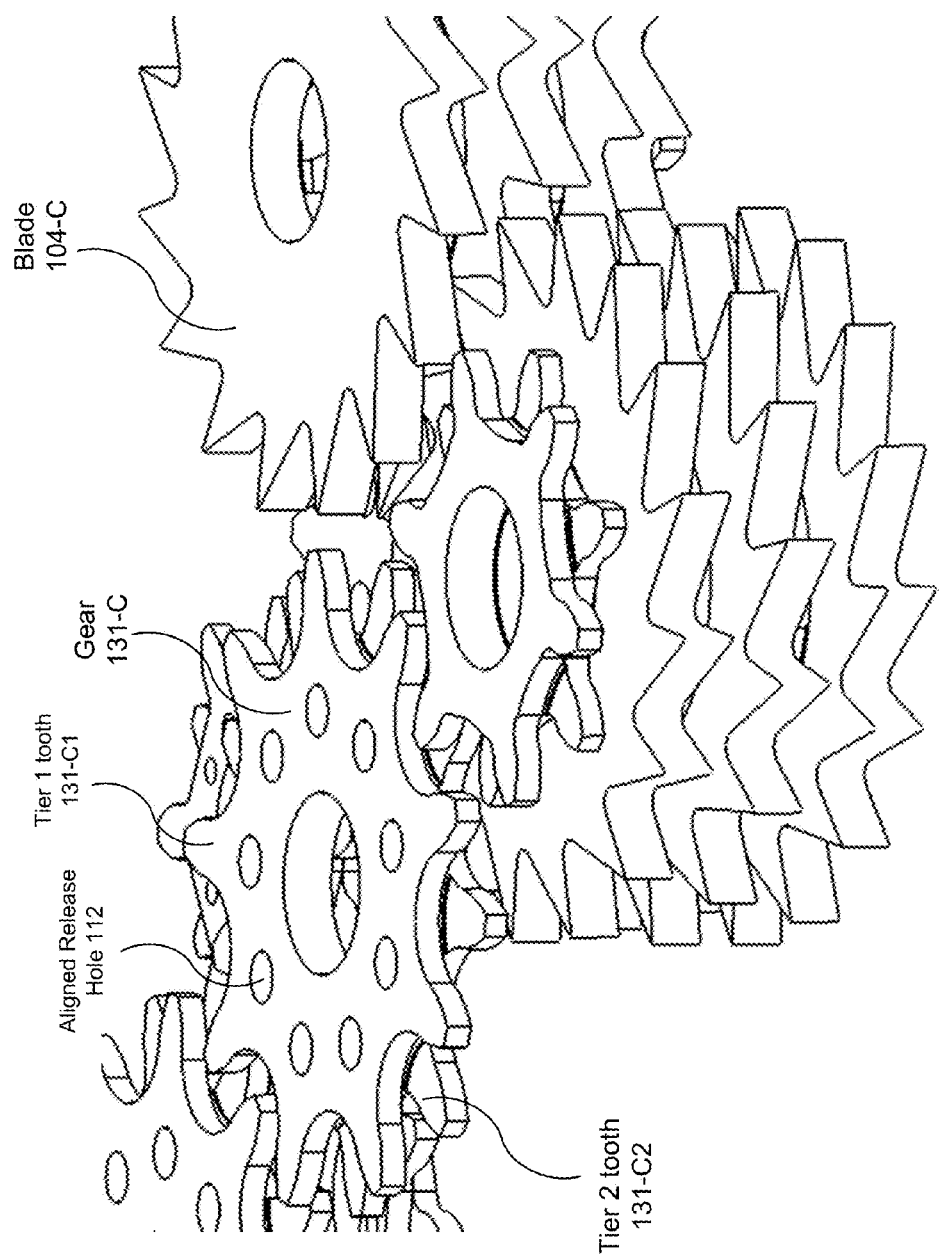
FIG. 14 provides a close up perspective view of a distal portion of the upper gear train and the cutting blades (which are driven thereby) according to the first embodiment.

FIGS. 5-15 provide various perspective views of a basic configuration of the device, tool, or instrument according to a first embodiment. The instrument 100 includes a housing 101, a plurality of blade stacks 102 and 104, each including a plurality of blades 102-A-102-C and 104-A-104-C, respectively, and two gear trains 131 and 141, including gears 131-A-131-D and 141-A-141-D, respectively (visible in FIG. 9). The gear trains are preferably covered by external housing 101 and internal enclosures 121 and 123 (e.g. as shown in FIG. 12. Gear trains 131 and 141 are used to transfer drive force to blade stacks 102 and 104 respectively. The proximal end of the gear trains 131 and 141 includes a drive shaft coupler 105 to allow actuation of the gear train 131 via upper drive gear 131-A and actuation of gear train 141 via lower drive gear 141-A, via a rotational force applied to the coupler via a rotating drive shaft (not shown). The instrument of this embodiment would be combined with other elements, such as motors, vacuum sources, irrigation sources, push tubes, pull wires, lumens, guide wires, and other navigation, control or visualization elements to provide complete instrument solution for performing medical procedures or other desired actions.

According to some embodiments of the invention the drive shaft may be powered by an electric motor located in proximity to the device, an electric motor located at the end of a flexible shaft drive wherein the motor is remote from the device (e.g. outside the body when the device is used at the end a catheter or other delivery lumen in a minimally invasive procedure. In other embodiments, e.g. the second embodiment, the device may be powered by a pulley and belt as shown in the FIGS. 16A and 16B. In an alternative to the second embodiment the device may be powered by a sprocket and chain (not shown). In still other embodiments, e.g. the third embodiment, the device may be powered via flow of a pneumatic fluid or a hydraulic fluid via one or more inlets, channels and outlets past an impeller as shown in FIG. 17. In some variations of the first-third embodiments, the impeller or drive shaft may be coupled to the coupler or gear trains via a plurality of additional gears or other elements that provide gear reduction to increase torque or to provide increased speed. In some embodiments, the drive shaft, not shown, may be furnished with a square distal end to engage the coupler, causing it to turn with the shaft. In some embodiments, the drive shaft may be surrounded by a sheath which may be affixed to the housing of the instrument.

In some alternative embodiments the drive shaft may extend a significant distant from the drive shaft coupler (e.g. perpendicular to the plane of the upper or lower faces of the housing, i.e. in the Z-direction or vertical direction relative to the planes of the layers (e.g. horizontal planes) used in forming the device via multi-layer, multi-material electrochemical fabrication methods. In other alternative embodiments the drive shaft may be coupled to a secondary shaft or flexible lead which extends in a direction parallel to the planes of the faces of the housing (e.g. proximally along the longitudinal axis of the device or radially relative to the longitudinal axis of the device).

Figure 5:
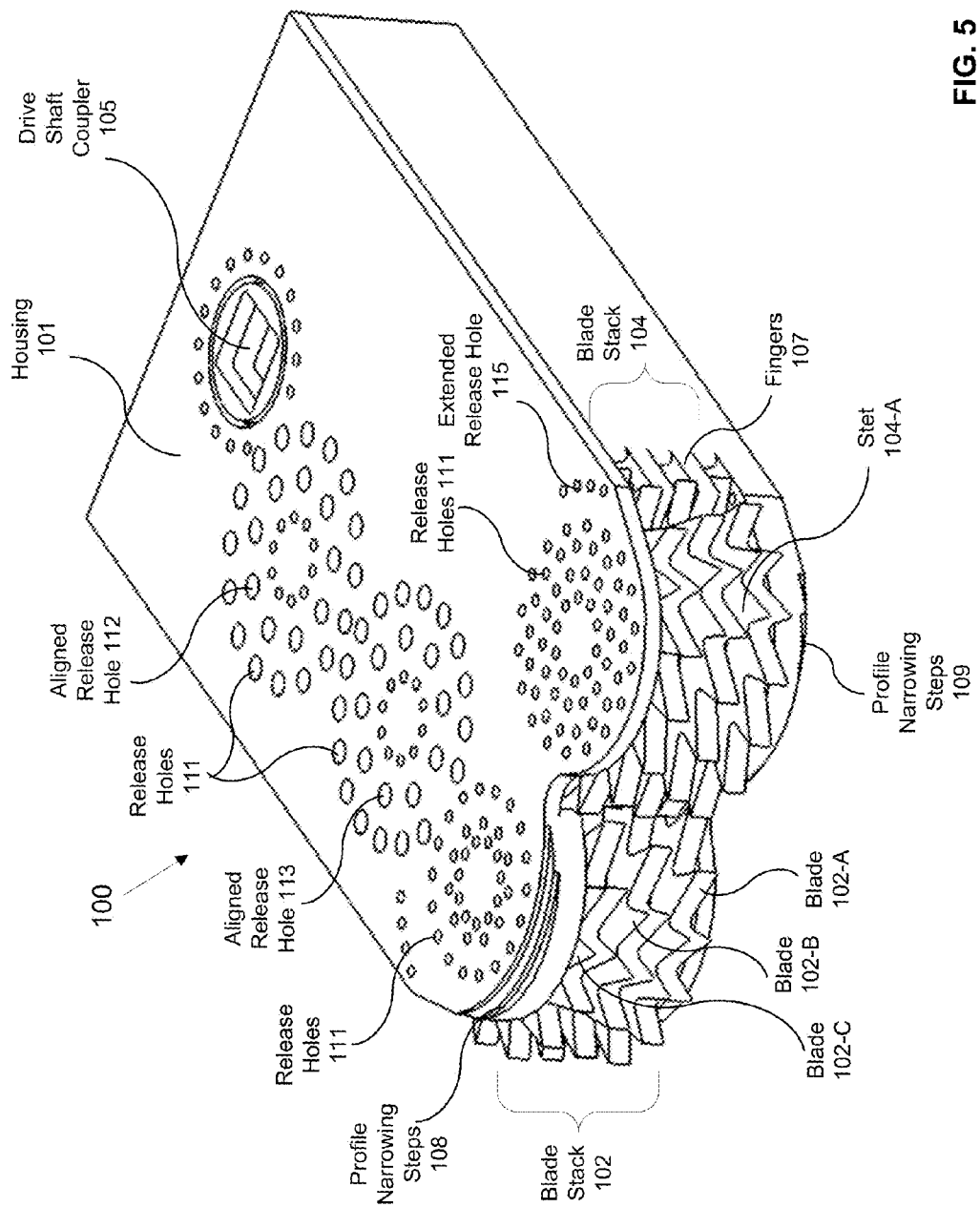
FIG. 5 provides an upper perspective view of a basic shredding device according to a first embodiment of the invention.
Figure 6:
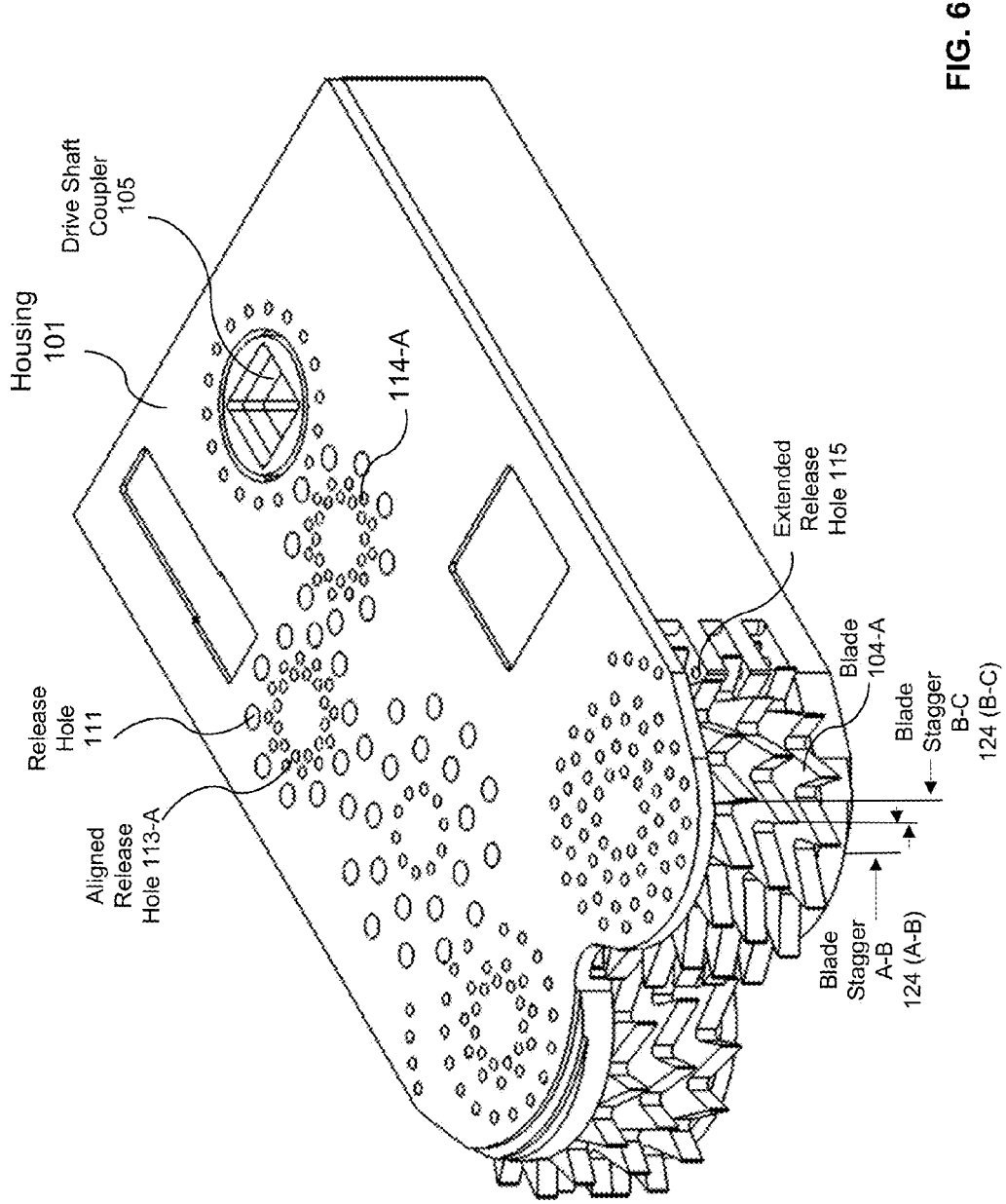
FIG. 6 provides a lower perspective view of a basic shredding device of according to the first embodiment where optional indentations have been provided in the housing surface for location of identification information or to acts as external interface elements.
Figure 7:
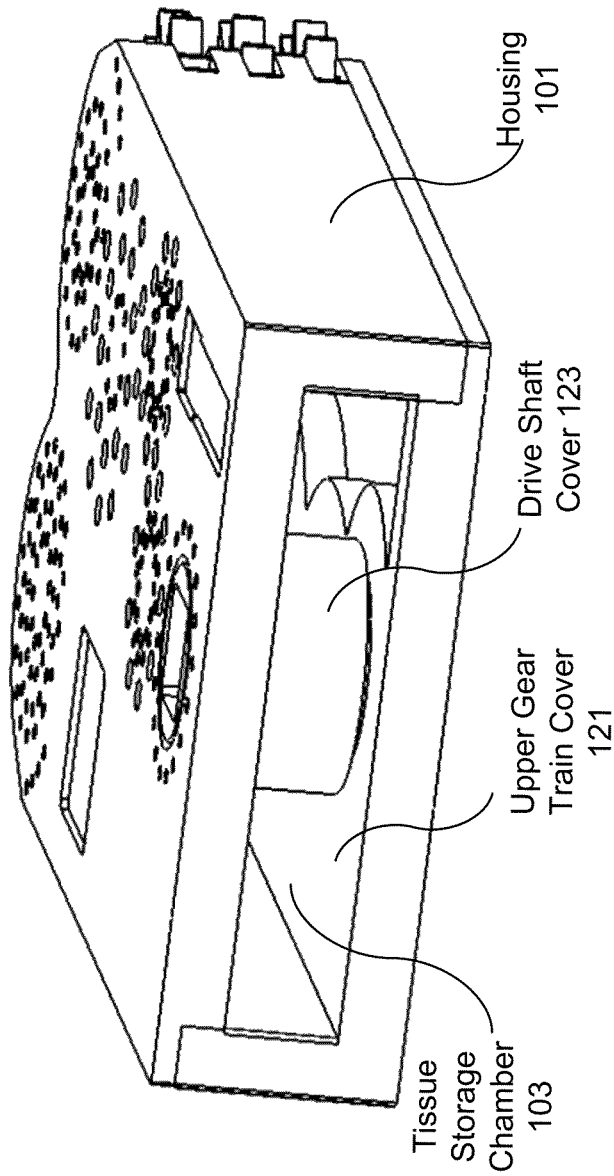
FIG. 7 provides a perspective view of a back end (i.e. proximal side) of the device of the first embodiment.
Figure 8:
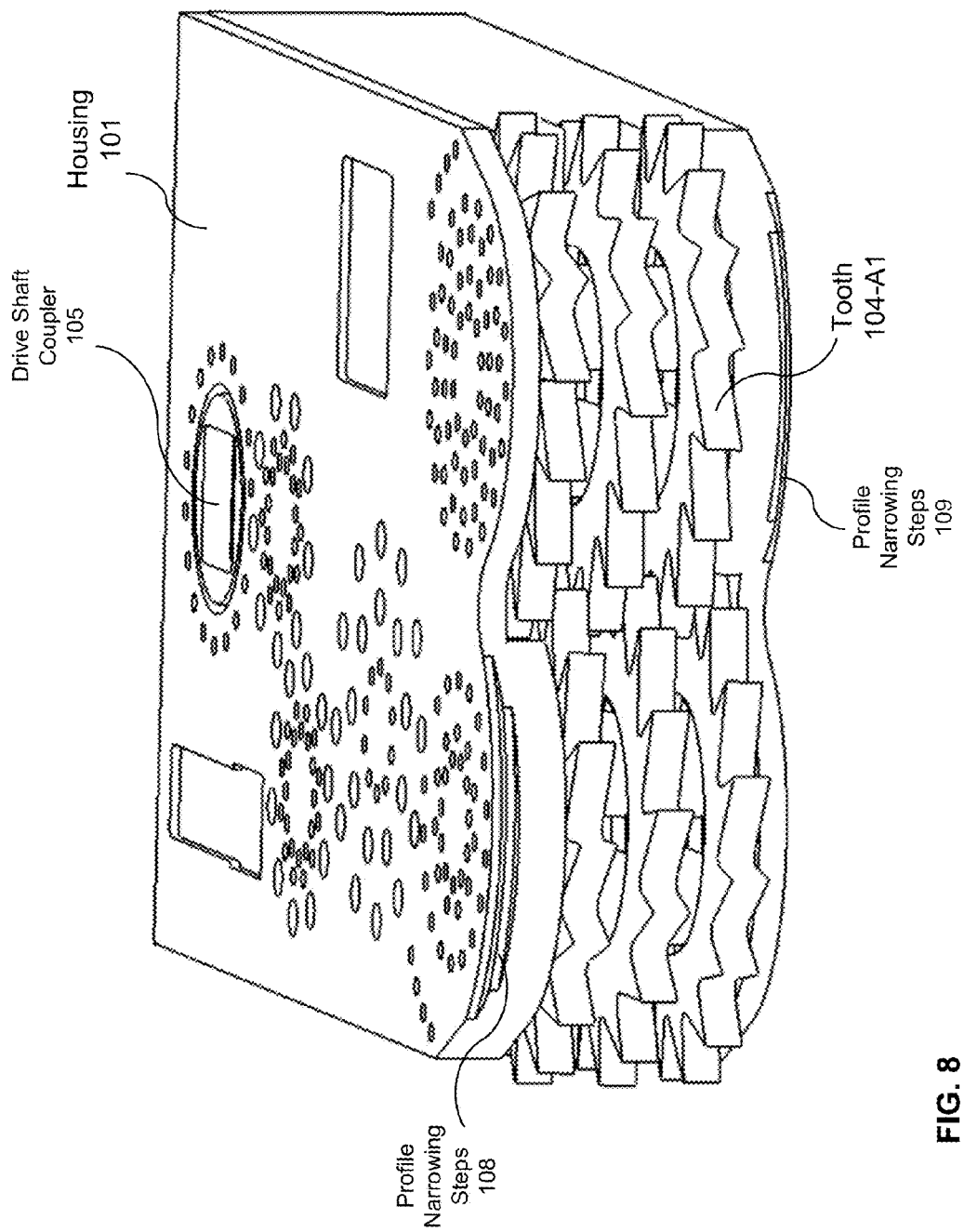
FIG. 8 provides a perspective view of the distal end of the device of the first embodiment.

FIGS. 5-6 provide general views showing opposite primary housing surfaces (e.g., top and bottom) of the instrument. In the proximal view of FIG. 7, the tissue storage chamber 103 is clearly visible. In the distal view of FIG. 8, the interdigitated blades of the instrument are clearly visible along with some star-stepping 108 and 109 of the left upper and right lower portions of the housing to minimize the height profile of the device.

Figure 9:
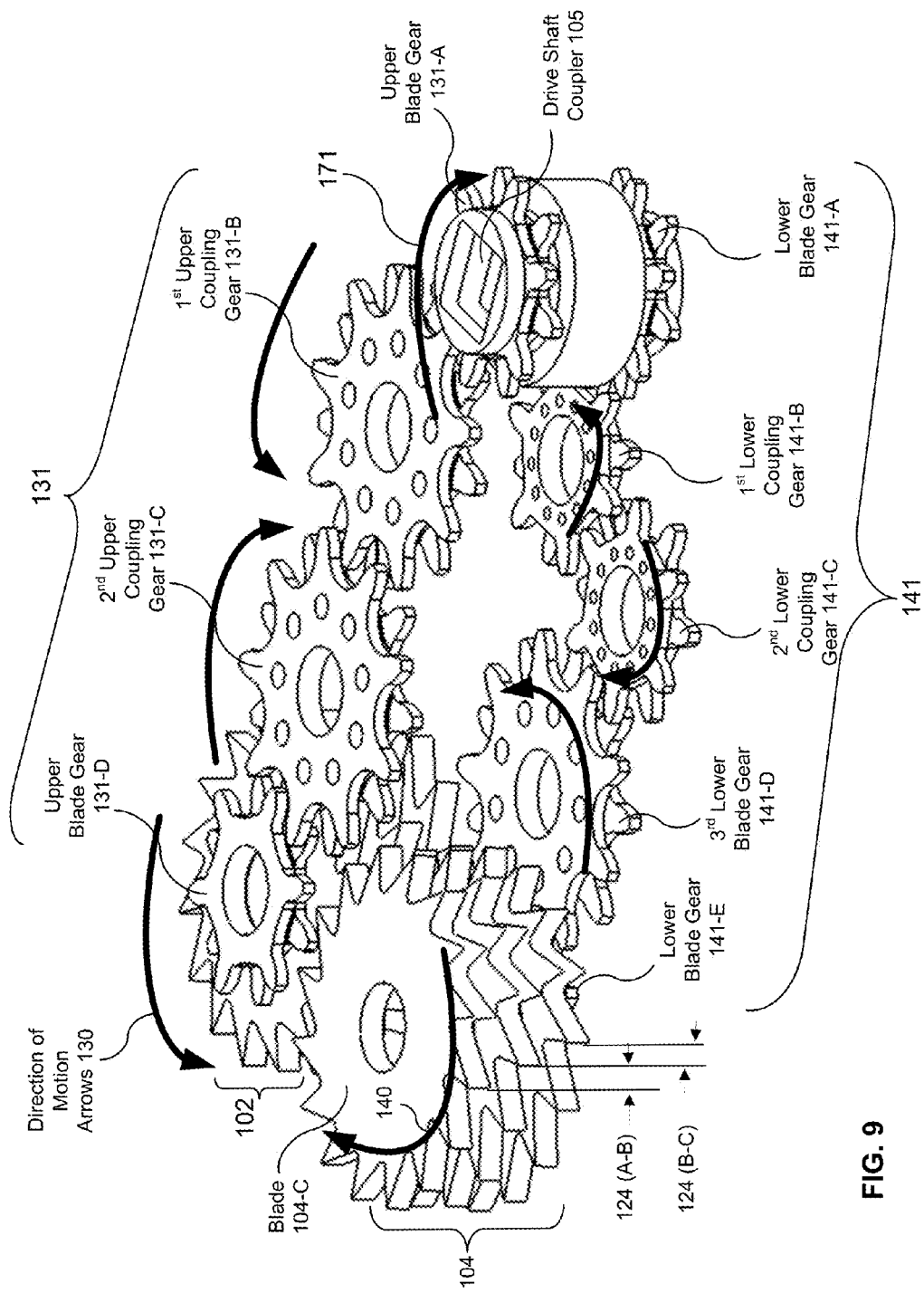
FIG. 9 provides a perspective side view of the gear train of the device of the first embodiment.

In the various embodiments of the invention, the cutting blades serve one or more purposes including, for example, tissue cutting, tissue tearing and tissue entrainment. Tissue entrainment may be provided to capture the tissue and convey it into a tissue storage chamber 103 within the body of the instrument or to an external storage chamber that may be accessed through the body of the instrument via a vacuum line or other extraction mechanism (e.g. Archimedes screw or other mechanical conveyor). In some embodiments, the blades are configured to optimize one or more of the above functions. In some embodiments, the blades may be configured to address the characteristics of a particular tissue type. The blades in each stack, as shown in FIG. 9 have their teeth staggered relative to neighboring blades by a fractional amount of the angular spacing of the successive teeth. For example the stagger between the teeth of blade 104-C and 104-B is 124(A-B) while that between 104-B and 104-A is 124(B-C). Though shown as a length portion of the blade circumference it could alternatively be expressed as an angular portion.

In some embodiments the blade tips, gear pins and other high wear surfaces may be formed from a wear resistant material while other portions of the device may be formed from another material that is more suited to the functionality of the device as a whole (e.g. a more resilient or less brittle material).

FIGS. 9-10 provide perspective views of the entire gear trains 131 and 141 such that their relationship may be understood. The gear trains serve at least two functions. A first function is to allow the drive shaft to be at a distance from the blades such that the instrument can plunge into the tissue in an unobstructed manner. A second function of the gear trains is to produce the opposing motion of the two blade stacks 102 and 104 such that they may be turned towards one another (i.e. centrally inward) when grinding and away from one another (i.e. centrally outward) if a jam should occur. During normal operation stack 102 turns counterclockwise and stack 104 turns clockwise as shown in FIG. 9, to create an inward-directed flow of tissue. In some variations of this embodiment, the blade stacks may be made to rotate at different rates to provide enhanced longitudinal shredding of tissue.

In FIGS. 9-10 the instrument or device housing 101 has been hidden from view. In the figures, it can be seen that the drive shaft coupler engages upper and lower sets of gears 131-A and 141-A. The upper set, including gears 131-A to 131-D which ultimately drive blade stack 102, while the lower set, including gears 141-A to 141-E ultimately driving blade stack 104. In FIG. 9, the drive shaft coupler is shown as being driven clockwise via arrow 171 which causes the stack of blades 102 driven by the upper gears 131 to be driven counterclockwise as shown by arrow 130. Meanwhile, the same rotation of the coupler 105 causes the stack of blades 104 driven by the lower gears 141 to be driven clockwise as shown by arrow 140. There are two gears in the upper set—not including gears that are attached to the coupler or the blade stacks—but three gears in the lower set. The extra gear in the lower set reverses the direction of rotation of one set of stacked blades with respect to the other. In alternative embodiments a all or a portion of the gears of the upper and/or lower sets may be replaced by chain or other flexible coupling elements and gears by sprockets or the like.

FIG. 11 shows the upper gear train 131, with gear 131-B labeled, but shows the lower gear train as being located below its shield or enclosure 121. This shielding serves to minimize exposure of the gear train to tissue and other contaminants which might impede operation of the gears. Similarly, the upper set of gears is also shielded within an enclosure 123 (see FIG. 12) which forms part of the housing. The tissue storage chamber is located between the two sets of gears and their enclosures. The shafts on which the gears, coupler, and blades turn are preferably integral with the housing. FIG. 12 also illustrates the section of gear 141-C exposes shaft 142-C around which gear 141-C rotates via a circular gaps (e.g. having an intralayer radial width greater than the minimum feature size). Also FIG. 12 illustrates that when gears 131B and 141C are in their as formed positions, they have etching holes 112-B and 114-B, respectively, that are aligned with etching holes 112-A and 114-A in housing 101 that allow more direct entry of etchant into the gear movement cavities defined by covers 122 and 121 in conjunction with housing 101 so that post-layer formation etching of sacrificial material can more readily occur from these cavities. In some embodiments partial alignment would be better than no alignment and offset of etching holes by no more than 2 mm or even 5 mm would be beneficial as compared to offsets which are significantly greater. FIG. 12 also shows a portion of blade shaft 103 around which blade stack 104 rotates. FIG. 12 along with FIG. 5 also shows interdigitated fingers 107 which are located between successive blade levels to inhibit the outflow of tissue drawing into cavity 103 as the blades tips rotate out of and then back into the housing. Such fingers, vacuum (i.e. suction applied to the proximal end of the working end), irrigation directed onto the blades within the housing (e.g. vertically downward or downward and proximally), or a combination of two or more of these elements may be useful in removing tissue from the blade and inhibiting its distal exit from the working end back into working area within the body of a patient. In some embodiments, it is desired to define a shearing thickness as the gap between elements has they move past one another. Such gaps may be defined by layer thickness increments, or multiple such increments, or by the intralayer spacing of elements as they move past one another. In some embodiments, shearing thickness of blades passing blades or blades moving past interdigitated fingers, or the like may be optimally set in the range of 2-100 microns or some other amount depending on the viscosity or other parameters of the materials being encounter and what the interaction is to be (e.g. tearing, shredding, transporting, or the like). For example for shredding or tearing the gap may be in the range of 2-10 microns and more preferably in the range of 4-6 microns.

Figure 15:
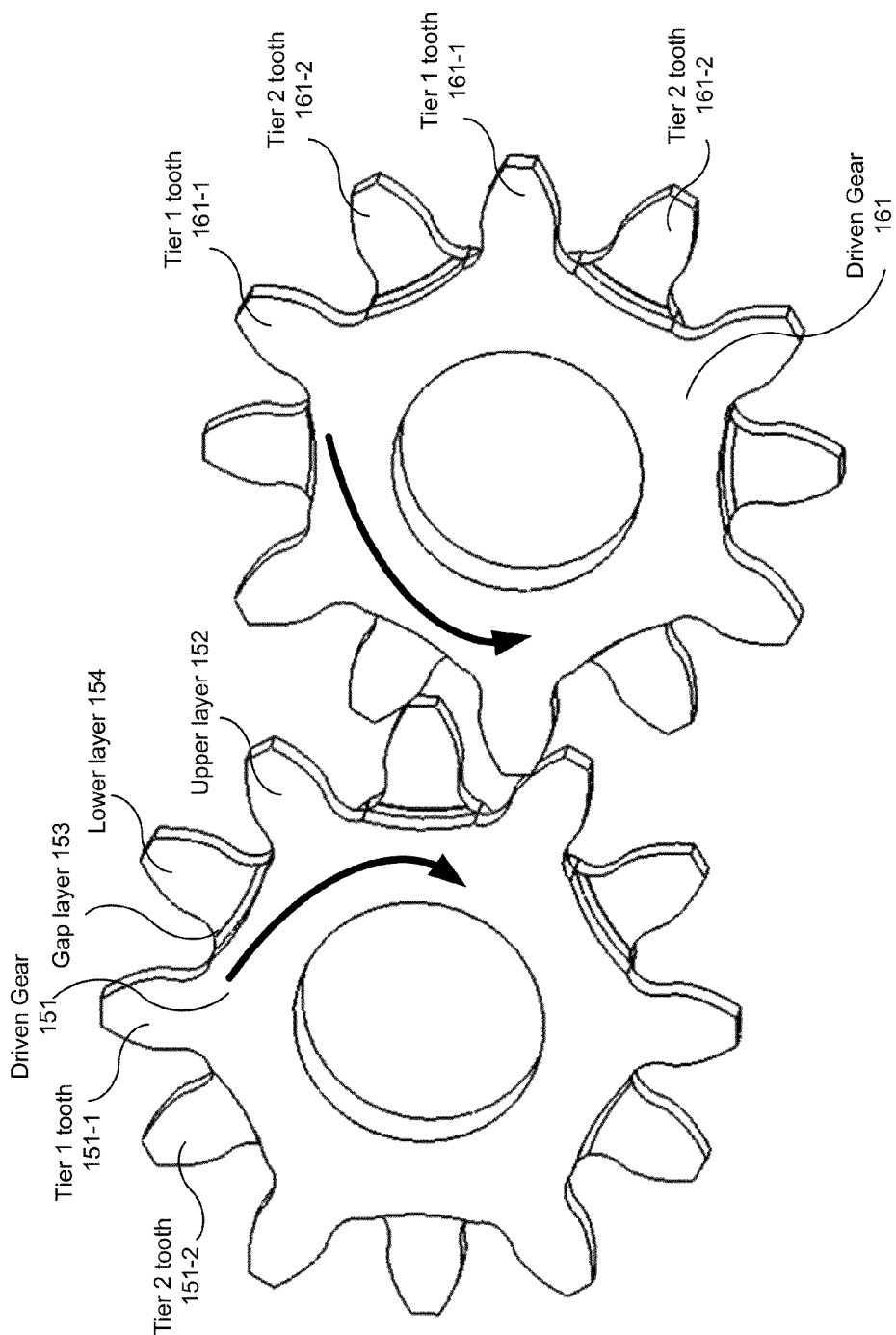
FIG. 15 provides a perspective view of two gears of the gear train of the first embodiment of the invention wherein each of two gears includes a multi-tier gear (i.e. three tiers in this example, lower gear tear, spacing tier, and upper gear tier) having different teeth orientations on different tiers to provide tighter gear meshing while maintaining desired single layer minimum feature size spacing.

The gears (most clearly from FIGS. 13-15) in the gear trains (131-B to 131C and 141-B to 141-D) as well as those attached to the coupler and the blades (131-A, 141-A, 131-D, and 141-E) have teeth on multiple tiers. This design enables fabrication of tightly-meshed gears while providing a minimum gap between elements on a single layer. In some embodiments, each tier is formed from a single multi-material layer while in other embodiments each tier is formed from multiple layers. In some embodiments, more than three tiers may be provided. In some embodiments, the relative thickness of teeth in each tier may vary. In the embodiment shown in the figures, each of the first and third tiers has half the number of teeth of the entire gear. When driven in one direction (e.g., as shown in FIG. 15), the gear still meshes properly and behaves as an involute spur gear. In operation, a tooth on tier 1 of the driving gear engages a tooth on tier 1 of the driven gear. This alternates, as the gears turn, with a tooth on tier 3 of the driving gear engaging a tooth on tier 3 of the driven gear. In some embodiments, the design of the teeth allows two teeth (one on tier 1 and one on tier 3) on the driving gear to always remain in contact with two teeth (one on tier 1 and one on tier 3) on the driven gear. As-fabricated, the gears are rotated such that distance between teeth is maximized, as in FIGS. 9-10. See FIG. 3. It is possible to drive the gear train in both directions; however, there is considerable backlash due to the distance between teeth on any given tier. In some embodiments, additional tiers may be added so that gear interfaces do not occur on only two levels but occur on three or more levels.

In forming the device of the first embodiment not only is it necessary to maintain horizontal spacing and dimensions of components above the minimum feature size, it is important that vertical gaps be formed between various components that overlap in XY space (assuming layers are being stacked along the Z axis) so that they do not inadvertently bond together and also ensure that adequate pathways are provided to allow etching solution to access and remove sacrificial material. In particular, it is important that gaps between the lower tier and upper tier gear exist so that upper and lower tiers of adjacent gears do not bond together. It is also important to place vertical gaps (e.g. via thin layers, e.g. 2-8 um each) between moving components and the housing and enclosure elements.

In some embodiments where additional tiers are provided, it may be possible to remove one or more of the immediate tiers (i.e. those that do not have gear teeth) as it may be possible to form gear teeth on multiple levels without any two consecutive levels having teeth that overlap in the XY plane in the as formed position.

Figure 16A:
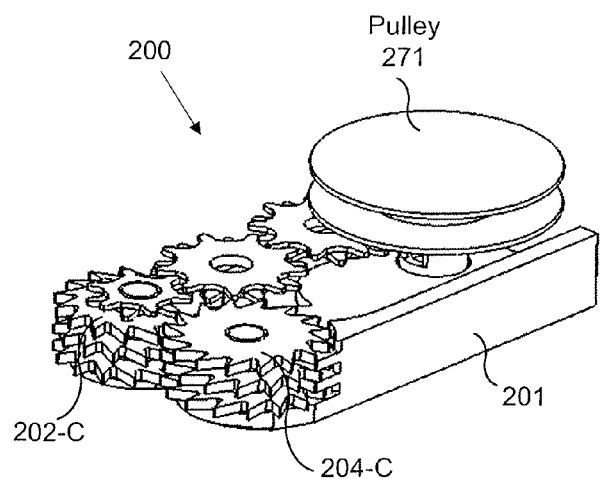
FIGS. 16A and 16B provide a perspective view of a device according to a second embodiment of the invention wherein an alternative drive mechanism is used which includes a pulley and a belt to provide rotational force to the gear train.
Figure 16B:
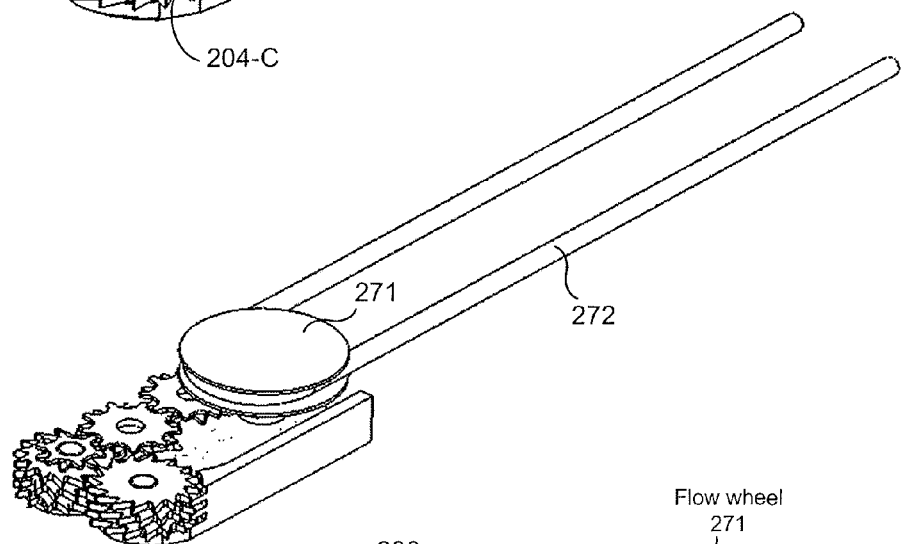
Figure 17:
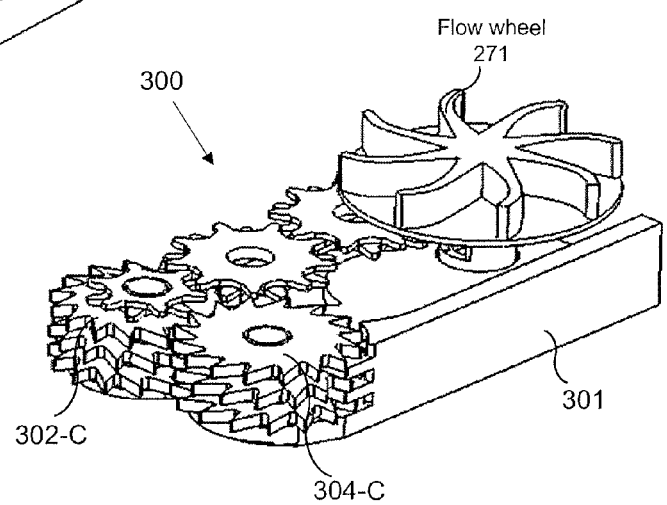
FIG. 17 provides a perspective view of a device according to a third embodiment of the invention wherein a different alternative drive mechanism is used which includes a fan or turbine blade which may be spun by liquid or gas via appropriate channels, inlets, and outlets (not shown).

FIGS. 16A and 16B a tool 200 of an alternative embodiment is depicted including a housing 200, blades 202-C and 204-C in separated blade stacks and a pulley 271 which may be powered by a belt 272 to drive the gear train.

FIG. 17 depicts an tool 300 of an alternative embodiment including a housing 300, blades 302-C and 304-C in separated blade stacks and an alternative drive mechanism in the form of fan blade 271 coupled to the gear chain (which may be spun by liquid or gas via appropriate inlet and outlet channels and paths.

In some alternative embodiments, it is possible to form portions of the device of the first embodiment separately and then assemble them but it is preferred to form the device as a whole in a fully assembled state. In some embodiments to improve etching of sacrificial material from components that move relative to each other they may be formed with fully or partially overlapping etching holes so that improved flow paths are created for removing sacrificial material.

In some embodiments the device of the first embodiment may formed with a length of about 4 mm, a width of about 2.5 mm and a height of about 0.75 to 1.0 mm. In other embodiments the height may be increased to several millimeters or decreased further, the length and width may be increased many times (3-5 to even 10 times) or even decreased.

In some embodiments gap layers (i.e. intermediate tiers) may be as little as 2 microns or as much as 10 microns with 4-6 microns being generally preferred while non-gap layers may be as large as 20-50 micron or more.

In using the device of the first embodiment, numerous alternative configurations and processes are possible, for example, the device may be combined in various ways with one or more push tubes, it may be feed down a lumen, it may be feed out the end of a lumen to a working area, it may be used in combination with expanders and/or distal protection devices, it may be used with only axial movement occurring during shredding, it may undergo rotational motion during shredding, it may undergo radial motion during shredding, it may be used in combination with forceps or claws to pull or push tissue toward the blades.

The drive mechanism may use universal joints, crown gears, or bevel gears coupled to drive gears and oriented so the drive train axis may be rotated to become parallel to the longitudinal axis of the device, or to otherwise lie perpendicular to the height of the device. Additional gears may be formed in the same orientation as those in the first embodiment and then rotated on bendable supports or pivotable supports to take on a desired orientation. In some embodiments the device may be part of a larger tool or instrument which includes a delivery mechanism and/or a lumen through which power can be transferred and/or which may include lumens for delivering irrigation fluid and or suction to remove entrained material or tissue that has been brought into the device.

In some uses of the device, the storage cavity may remain open while in other embodiments it may be closed while in still other embodiments it may pass items smaller than a given size (e.g. via a filter or the like). After removal of the device from a working area, the device may be emptied of collected tissue via a door or other release mechanism.

In some embodiments, etching holes may be sealed after release of sacrificial material. In some embodiments, blades may be tapered to drive material toward the central blade of a gear stack.

In some embodiments a fluid inlet and exit ports may exist for flushing out material which entered the device during operation.

In some embodiments, blade stacks may rotate at different rates or blades within a single stack may rotate at different rates.

FIGS. 18-21 depict a number of additional embodiments in which single modifications have been made to the basic configuration shown in FIG. 5. In some further embodiments, combinations of these and related modifications would be used.

In some embodiments, as in the device, tool, or instrument 400 of FIGS. 18A and 18B, including housing 401 and blades 404, the instrument comprises 'hybrid' blades with teeth that are capable of both piercing and cutting into tissue to entrain it. The outer portions of the teeth or more simply the outer teeth 404-1 and 404-2 are intended to cut the tissue, while the inner or middle portion 404-2 are intended to entrain the cut tissue and convey it into the instrument. In some embodiments, the outer portions 404-1 and 404-2 are thinner (e.g., formed from a single thin layer in a multi-material, multi-layer electrochemical fabrication process) and the inner portion 404-2 is thicker (e.g., formed from one or more thicker layers). In some alternative embodiments the blade may have a non-symmetric shape based on the intended directions of motion and use.

Figure 19:
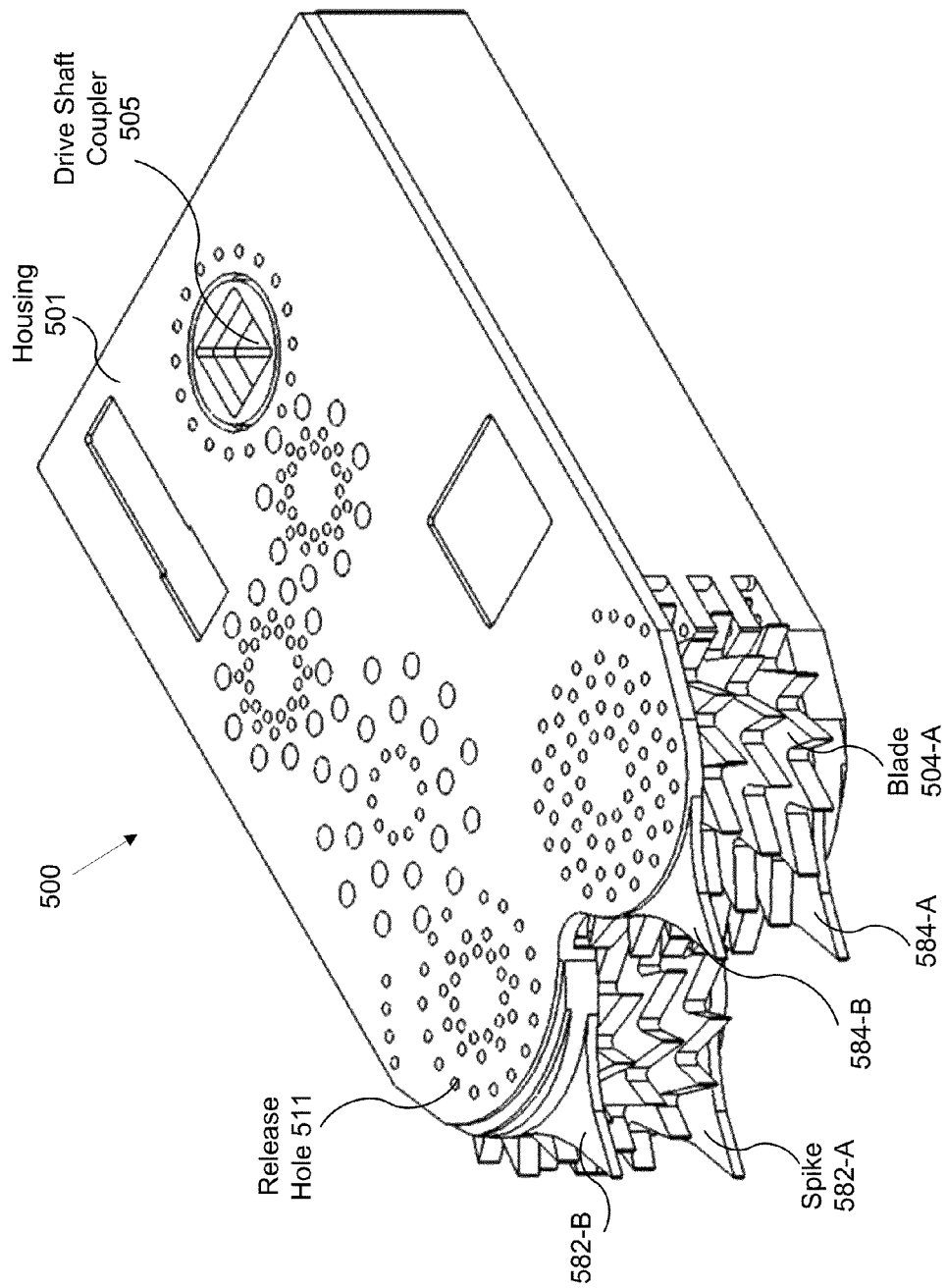
FIG. 19 shows an overview of an embodiment of the invention comprising distal spikes.
Figure 20:
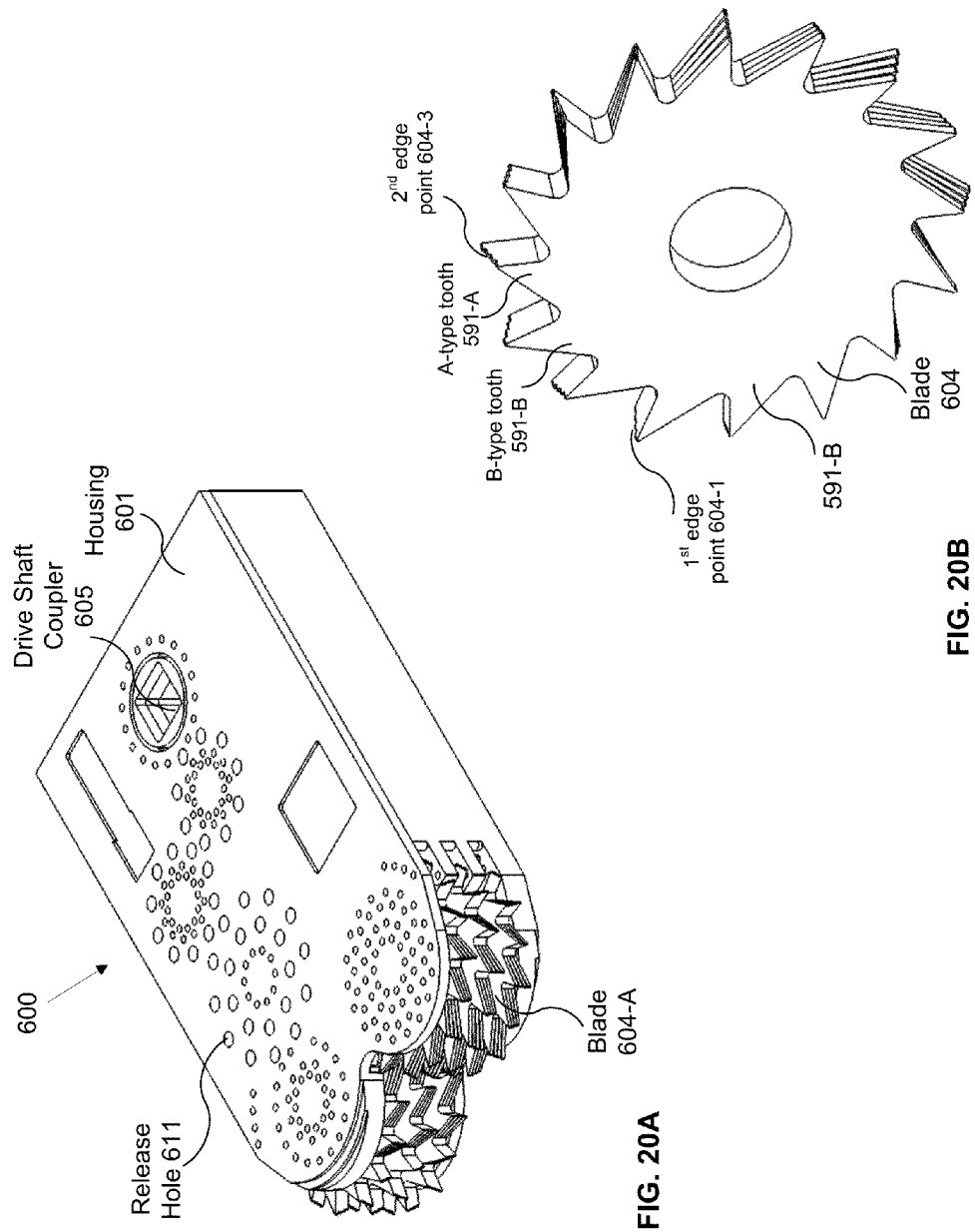
FIGS. 20A and 20B shows an overview of an embodiment of the invention comprising cutting/piercing teeth.

In some embodiments, as in the device, tool, or instrument 500 of FIG. 19, the instrument may include at least one spike (e.g. one of spikes 584-A, 584-B, 582-A, and 582-B) to stabilize its position during use. The spikes pierce the tissue prior to the blades engaging the tissue, resisting any tendency of the instrument to be pushed, e.g. by the interaction of the blades with the tissue, in a direction different from that desired (e.g., directly into the tissue).

In some embodiments, as in the device, tool, or instrument 600 of FIGS. 20A and 20B having a housing 601 and blades 604 with teeth 591 that have a sharpened point. In some embodiments as shown, the point alternates from one surface of the blade to the other (i.e. on the back side or plane of the blade teeth designated by 591-A having edge points 604-3 and on the front side or plane of the blade teeth designated 591-B and having edge points 604-1. In some embodiments, the alternation period is one tooth, while in other embodiments, it is more than one tooth or is even aperiodic. Blades with such points may be advantageous in cutting into or piercing tissue that would otherwise resist cutting, although their ability to entrain tissue may be inferior to blades with flat teeth such as those of FIG. 5. In FIGS. 20A and 20B, the teeth are shown with stair steps as they would normally be if fabricated using a multi-layer multi-material electrochemical fabrication process. However, in some embodiments, the edge of the teeth does not have such stair steps.

Figure 21:
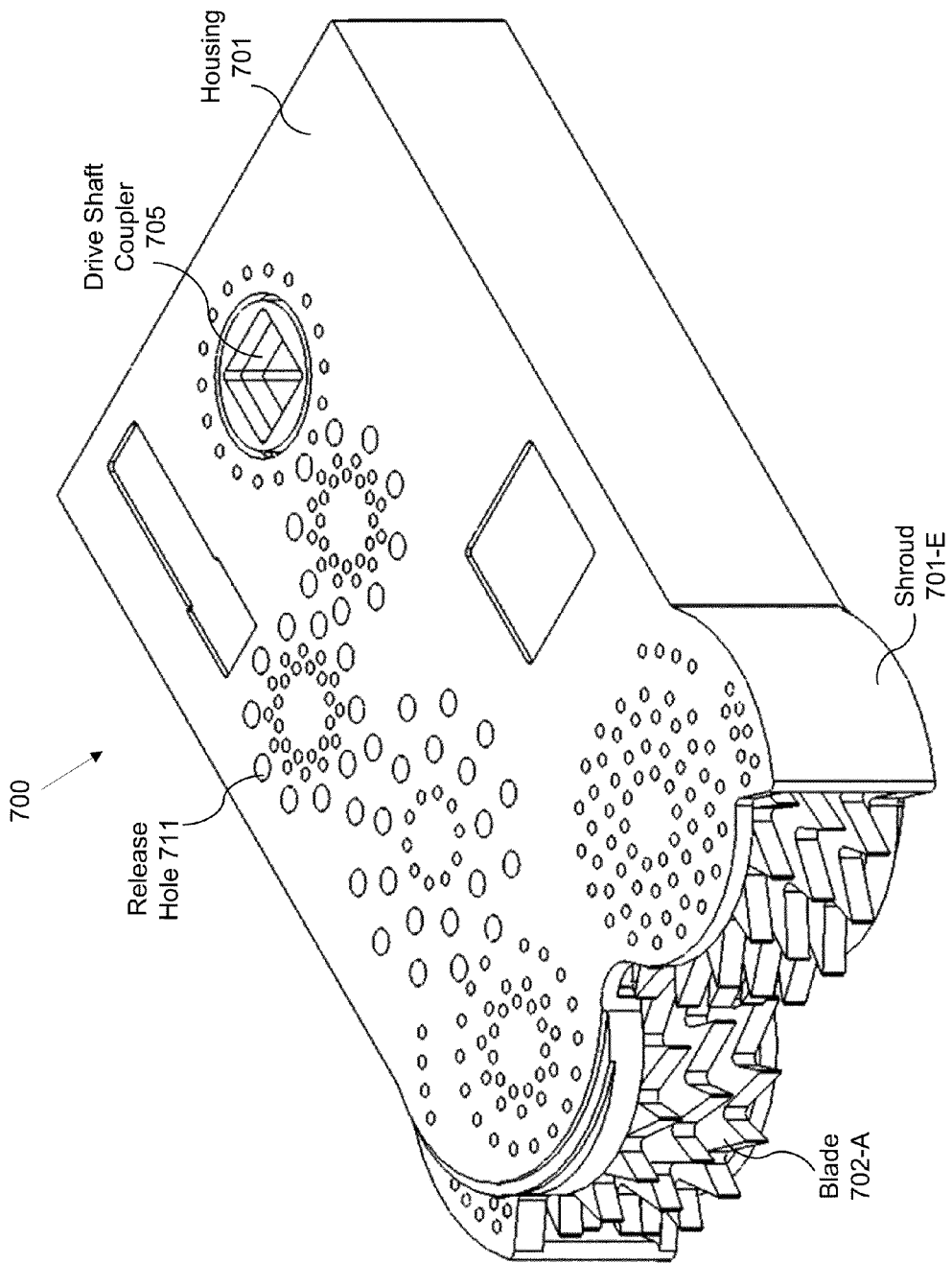
FIG. 21 shows an embodiment of the invention comprising shrouded blades.

In some embodiments, such as that of the device, tool, or instrument 700 as shown in FIG. 21, the instrument includes shrouds 701-E on the sides of the housing 701. These serve at least two purposes. A primary purpose is to minimize the release of tissue or other material (i.e. out flow of tissue or other material that has been brought into the housing of the tool) from the side of the blades, since release during a surgical procedure is in many cases undesirable. A secondary purpose is to limit the tissue that is processed by the instrument to the region directly in front of the instrument. The tissue to the side of the instrument is pushed aside rather than interacting with the blades (i.e. being cut or shredded by the blades, being pulled into the housing, and/or being otherwise disrupted by the blades).

In some embodiments of the instrument, holes, textures, grooves, or other features are added to the rotating elements or the shafts on which they rotate, or to the surfaces surrounding the rotating elements. Such features may serve to create aerodynamic or hydrodynamic bearing surfaces that reduce friction during rotation of the elements.

FURTHER COMMENTS AND CONCLUSIONS

Structural or sacrificial dielectric materials may be incorporated into embodiments of the present invention in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., now abandoned, and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384 which was filed May 7, 2004 by Cohen et al. which is entitled "Method of Electrochemically Fabricating Multilayer Structures Having Improved Interlayer Adhesion" and which is hereby incorporated herein by reference as if set forth in full. This application is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. Patent Application No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, entitled Methods of and Apparatus for Electrochemically Fabricating Structures Via Interlaced Layers or Via Selective Etching and Filling of Voids, now abandoned. The techniques disclosed in this referenced application may be combined with the techniques and alternatives set forth explicitly herein to derive additional alternative embodiments. In particular, the structural features are still defined on a planar-layer-by-planar-layer basis but material associated with some layers are formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full. The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| U.S. Pat. Application No., Filing Date<br>U.S. Application Pub No., Pub Date<br>U.S. Pat. No., Issue Date | Inventor, Title |
| --- | --- |
| 09/493,496 - Jan. 28, 2000<br>—<br>PAT 6,790,377 - Sep. 14, 2004 | Cohen, "Method For Electrochemical Fabrication" |
| 10/677,556 - Oct. 1, 2003<br>2004-0134772 - Jul. 15, 2004 | Cohen, "Monolithic Structures Including Alignment and/or Retention Fixtures for Accepting Components" |
| 10/830,262 - Apr. 21, 2004<br>2004-0251142A - Dec. 16, 2004<br>PAT 7,198,704 - Apr. 3, 2007 | Cohen, "Methods of Reducing Interlayer Discontinuities in Electrochemically Fabricated Three-Dimensional Structures" |
| 10/271,574 - Oct. 15, 2002<br>2003-0127336A - July 10, 2003 | Cohen, "Methods of and Apparatus for Making High Aspect Ratio Microelectromechanical |

| U.S. Pat. Application No., Filing Date U.S. Application Pub No., Pub Date U.S. Pat. No., Issue Date | Inventor, Title |
|---|---|
| PAT 7,288,178 - Oct. 30, 2007 10/697,597 - Dec. 20, 2002 2004-0146650A - Jul. 29, 2004 | Structures" Lockard, "EFAB Methods and Apparatus Including Spray Metal or Powder Coating Processes" |
| 10/677,498 - Oct. 1, 2003 2004-0134788 - Jul. 15, 2004 PAT 7,235,166 - Jun. 26, 2007 | Cohen, "Multi-cell Masks and Methods and Apparatus for Using Such Masks To Form Three-Dimensional Structures" |
| 10/724,513 - Nov. 26, 2003 2004-0147124 - Jul. 29, 2004 PAT 7,368,044 - May 6, 2008 | Cohen, "Non-Conformable Masks and Methods and Apparatus for Forming Three-Dimensional Structures" |
| 10/607,931 - Jun. 27, 2003 2004-0140862 - Jul. 22, 2004 PAT 7,239,219 - Jul. 3, 2007 | Brown, "Miniature RF and Microwave Components and Methods for Fabricating Such Components" |
| 10/841,100 - May 7, 2004 2005-0032362 - Feb. 10, 2005 PAT 7,109,118 - Sep. 19, 2006 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 2004-0065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 PAT 7,229,542 - Jun. 12, 2007 | Bang, "Methods of and Apparatus for Molding Structures Using Sacrificial Metal Patterns" |
| 10/434,103 - May 7, 2004 2004-0020782A - Feb. 5, 2004 PAT 7,160,429 - Jan. 9, 2007 | Cohen, "Electrochemically Fabricated Hermetically Sealed Microstructures and Methods of and Apparatus for Producing Such Structures" |
| 10/841,006 - May 7, 2004 2005-0067292 - May 31, 2005 | Thompson, "Electrochemically Fabricated Structures Having Dielectric or Active Bases and Methods of and Apparatus for Producing Such Structures" |
| 10/434,519 - May 7, 2003 2004-0007470A - Jan. 15, 2004 PAT 7,252,861 - Aug. 7, 2007 | Smalley, "Methods of and Apparatus for Electro-chemically Fabricating Structures Via Interlaced Layers or Via Selective Etching and Filling of Voids" |
| 10/724,515 - Nov. 26, 2003 2004-0182716 - Sep. 23, 2004 PAT 7,291,254 - Nov. 6, 2007 | Cohen, "Method for Electrochemically Forming Structures Including Non-Parallel Mating of Contact Masks and Substrates" |
| 10/841,347 - May 7, 2004 2005-0072681 - Apr. 7, 2005 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733,195 - Apr. 9, 2007 2008-0050524 - Feb. 28, 2008 | Kumar, "Methods of Forming Three-Dimensional Structures Having Reduced Stress and/or Curvature" |
| 11/506,586 - Aug. 8, 2006 2007-0039828 - Feb. 22, 2007 | Cohen, "Mesoscale and Microscale Device Fabrication Methods Using Split Structures and Alignment Elements" |
| 10/949,744 - Sep. 24, 2004 2005-0126916 - Jun. 16, 2005 PAT 7,498,714 - Mar. 3, 2009 | Lockard, "Three-Dimensional Structures Having Feature Sizes Smaller Than a Minimum Feature Size and Methods for Fabricating" |

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A medical procedure comprising:
   a. insertion of a shredding tool into a working area associated with a body of a patient, the shredding tool comprising:
      i. a housing having a distal end and a proximal end;
      ii. a first multi-blade blade stack mounted for rotational motion about a first rotational axis relative to the housing, the first stack extending in part from the housing, the first stack comprising a plurality of substantially planar blades arranged in a parallel manner and co-axially along the first rotational axis, wherein at least one of the blades of the first stack comprises a first side and a second side parallel to and offset from the first side, and a plurality of cutting tips, wherein each cutting tip has dimensions, each of which are no greater than about 0.5 millimeters, wherein a maximum radial extension of at least some of the tips are located on the first side of the blade while the maximum radial extension of at least some other tips are located on the second side of the blade;
      iii. a second multi-blade blade stack mounted for rotational motion, about a second axis which is parallel to the first axis, relative to the housing and extending in part from the housing, wherein at least a portion of the blades of the second blade stack have interlaced positions with the blades of the first stack in a plane perpendicular to the first and second axes of rotation but which are offset in the direction of the first and second axes so that the blades of first stack do not interfere with the blades of the second stack;
      iv. a drive mechanism for rotating the blades of the first stack; and
      v. a drive mechanism for rotating the blades of the second stack in an opposite direction relative to the rotation of the blades of the first stacks;
   b. powering on the drive mechanism and moving the shredding tool to desired locations within the working area to intake and shred selected material; and
   c. extracting the shredding tool from the working area and from the body of the patient.

2. The procedure of claim 1 wherein the at least some of the tips of the shredding tool alternate around a circumference of the blade with the at least some other tips.

3. The procedure of claim 1 wherein the first multi-blade blade stack comprises a plurality of first circular blades with first cutting elements extending from circumferences of the first circular blades,
   wherein the second multi-blade blade stack comprises a plurality of second circular blades with second cutting elements extending from circumferences of the second circular blades,
   wherein each of the first circular blades rotates about a first common axis,
   wherein each of the second circular blades rotates about a second common axis,
   wherein the first circular blades each have a first thickness and a first gap relative to an immediate neighboring first circular blade,
   wherein the second circular blade each have a second thickness and a second gap relative to an immediate neighboring second circular blade,
   wherein the first thickness relative to the second gap and the second thickness relative to the first gap, allows interlacing and movement of the first and second blades while providing for intake and shredding of material encountered by the first and second blades during the medical procedure.

4. The procedure of claim 1 wherein the shredding tool comprises a plurality of stacked and adhered layers of deposited material.

5. The procedure of claim 4 wherein the plurality of stacked and adhered layers of deposited material comprise electrodeposited material.

6. The procedure of claim 1 wherein the medical procedure is a minimally invasive procedure.

7. The procedure of claim 1 wherein the material comprises tissue.

8. The procedure of claim 1 wherein the maximum radial extension alternates between the first side and the second side of the blade with an alternation period of one tooth.

9. The procedure of claim 1 wherein the maximum radial extension alternates between the first side and the second side of the blade with an alternation period of more than one tooth.

10. The procedure of claim 1 wherein the maximum radial extension alternates between the first side and the second side of the blade with an alternation period that is aperiodic.

* * * * *